(12) United States Patent
Mhuircheartaigh et al.

(10) Patent No.: US 12,114,987 B2
(45) Date of Patent: Oct. 15, 2024

(54) PERCEPTION LOSS DETECTION

(71) Applicant: OXFORD UNIVERSITY INNOVATION LIMITED, Oxford (GB)

(72) Inventors: Roisin Judith Ni Mhuircheartaigh, Dublin (IE); Irene Tracey, Headington (GB); Katie Warnaby, Headington (GB); Saad Jbabdi, Headington (GB); Richard Rogers, Headington (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 1307 days.

(21) Appl. No.: 16/720,507

(22) Filed: Dec. 19, 2019

(65) Prior Publication Data
US 2020/0196888 A1 Jun. 25, 2020

Related U.S. Application Data

(63) Continuation of application No. 14/404,337, filed as application No. PCT/GB2013/051445 on May 30, 2013, now Pat. No. 10,542,905.
(Continued)

(30) Foreign Application Priority Data

May 30, 2012 (GB) ..................... 1209638

(51) Int. Cl.
*A61B 5/374* (2021.01)
*A61B 5/00* (2006.01)
*A61M 5/172* (2006.01)

(52) U.S. Cl.
CPC ............ *A61B 5/374* (2021.01); *A61B 5/4821* (2013.01); *A61B 5/4839* (2013.01); *A61B 5/6803* (2013.01); *A61M 5/1723* (2013.01)

(58) Field of Classification Search
CPC ..... A61B 5/374; A61B 5/4821; A61B 5/4839; A61B 5/6803; A61B 5/40; A61B 5/446;
(Continued)

(56) References Cited

U.S. PATENT DOCUMENTS 5,320,109 A 6/1994 Chamoun et al.
5,775,330 A 7/1998 Kangas et al.
(Continued)

FOREIGN PATENT DOCUMENTS

CN 1538823 A 10/2004
CN 101081164 A 12/2007
(Continued)

OTHER PUBLICATIONS

Patent Examination Report issued by IP Australia on Nov. 12, 2016 regarding corresponding Patent No. 2013269331 (3 pages).
(Continued)

*Primary Examiner* — Navin Natnithithadha
(74) *Attorney, Agent, or Firm* — Harness, Dickey & Pierce, P.L.C.

(57) ABSTRACT

The present invention relates to a device for detecting a state of true perception loss of a human, the device including processing means operable to detect from information on electrical signals sensed adjacent to the scalp of the human the activity of oscillations present in the electrical signals as a marker for the state of true perception loss of the human.

20 Claims, 18 Drawing Sheets

Related U.S. Application Data

(60) Provisional application No. 61/746,975, filed on Dec. 28, 2012.

(58) Field of Classification Search
CPC ... A61B 5/4806; A61B 5/6831; A61M 5/1723
USPC .................................................. 600/544, 545
See application file for complete search history.

(56) References Cited

U.S. PATENT DOCUMENTS

| | | | |
|---|---|---|---|
| 6,067,467 | A | 5/2000 | John |
| 2002/0117176 | A1 | 8/2002 | Mantzaridis et al. |
| 2006/0167368 | A1 | 7/2006 | Sarkela |
| 2008/0177197 | A1 | 7/2008 | Lee et al. |
| 2009/0198145 | A1 | 8/2009 | Chow |
| 2009/0259136 | A1 | 10/2009 | Schieb |
| 2011/0125046 | A1 | 5/2011 | Burton et al. |
| 2012/0010591 | A1 | 1/2012 | Chazot et al. |
| 2014/0187973 | A1 | 7/2014 | Brown et al. |

FOREIGN PATENT DOCUMENTS

| | | | | |
|---|---|---|---|---|
| CN | 101301196 | A | | 11/2008 |
| CN | 101557855 | A | * | 10/2009 ............ A61M 21/02 |
| CN | 101677774 | A | | 3/2010 |
| CN | 103793593 | A | * | 5/2014 ............ A61B 5/0002 |
| GB | 2359367 | A | | 8/2001 |
| JP | 2006-255134 | A | | 9/2006 |

OTHER PUBLICATIONS

First Office Action issued by State Intellectual Property Office (SIPO) of People's Republic of China on Feb. 3, 2016 regarding corresponding Patent Application No. 201380037951.X (17 pages).
Second Office Action issued by State Intellectual Property Office (SIPO) of People's Republic of China on Aug. 26, 2016 regarding corresponding Patent Application No. 201380037951.X (5 pages).
Japanese Rejection Notice dated Mar. 30, 2017 (with English translation) regarding corresponding Japanese Application 2015-514592 (17 pages).
Lionel J. Velly, et al. "Differential Dynamic of Action on Cortical and Subcortical Structures of Anesthetic Agents During Induction of Anesthesia". Anesthesiology, Aug. 2007, vol. 107, No. 2, pp. 202-212 (11 pages).
Ira J. Rampil. "A Primer for EEG Signal Processing in Anesthesia". Anethesiology, American Society of Anesthesiologists, Inc., Oct. 1998, vol. 89, No. 4, pp. 980-1002 (23 pages).
Rejection Decision dated Apr. 19, 2017 issued by the State Intellectual Property Office of People's Republic of China (SIPO) regarding Application No. 201380037951 (with translation) (10 pages).
Re-Examination Decision dated Aug. 15, 2017 regarding Application No. 201380037951 revoking the rejection decision and returning the application to SIPO for further examination (without translation) (1 page).
Third Office Action dated Sep. 1, 2017 issued by State Intellectual Property Office of People's Republic of China (SIPO) regarding Application No. 201380037951 (with translation) (7 pages).
International Search Report and Written Opinion (both in English) for PCT/GB2013/051445, mailed Oct. 23, 2013; ISA/EP.
United Kingdom Search Report (in English) for GB 1209638.4, dated Sep. 13, 2012.
Molaee-Ardekani "Delta waves differently modulate high frequency components of EEG oscillations in various unconsciousness levels" Conference of the IEEE EMBS dated Aug. 23-26, 2007 (pp. 1295-1297).
Examination Report for PCT Appl. No. 13 734 140.0-1115 dated Jul. 30, 2020 (6 pages).

* cited by examiner

Time in minutes

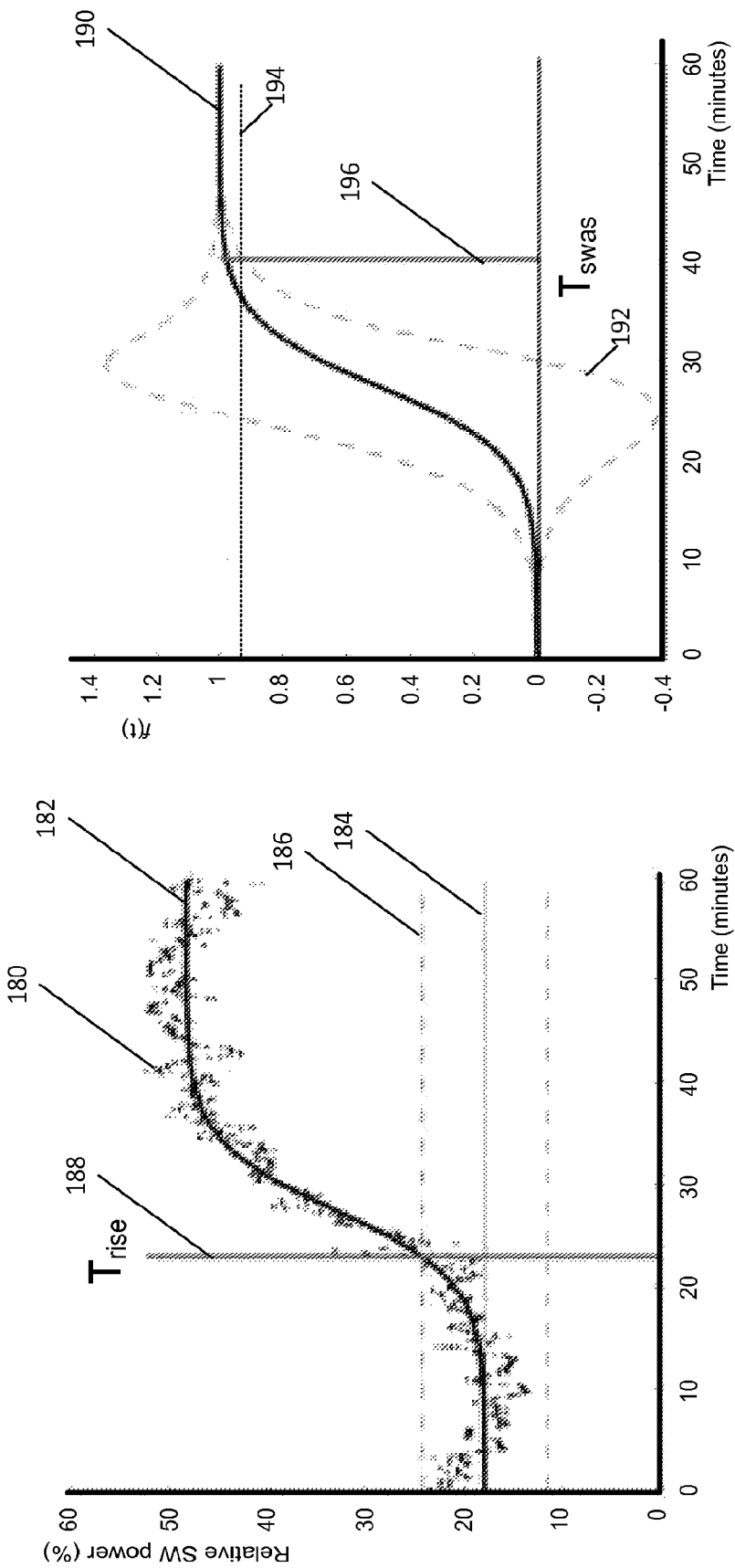

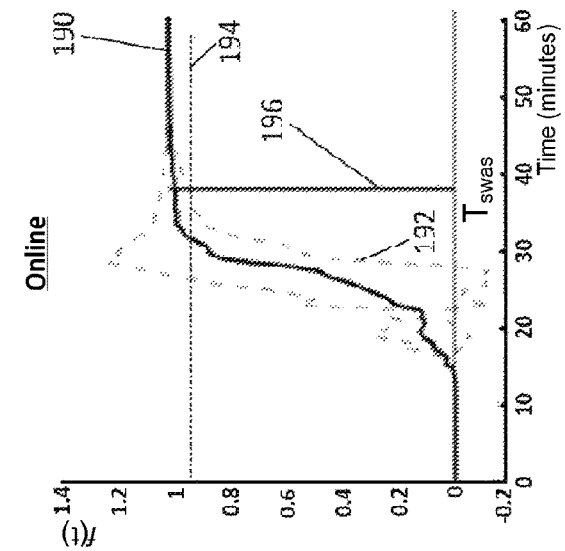
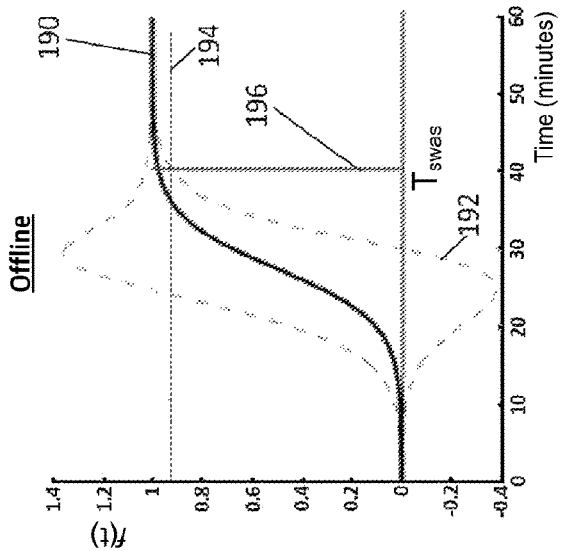
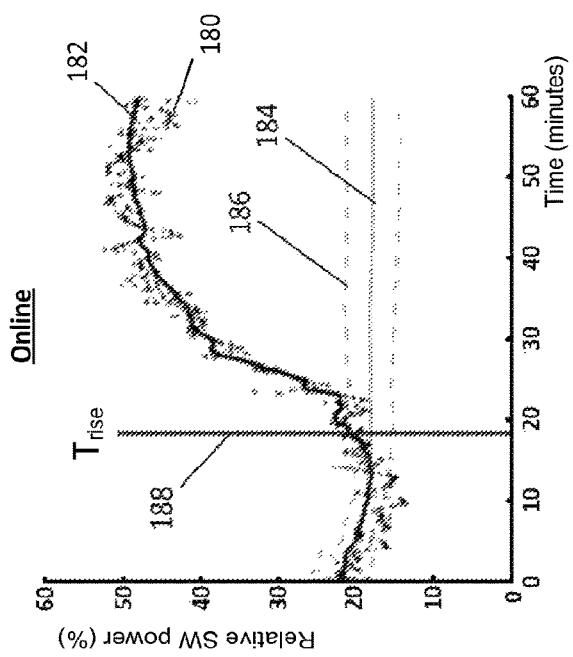
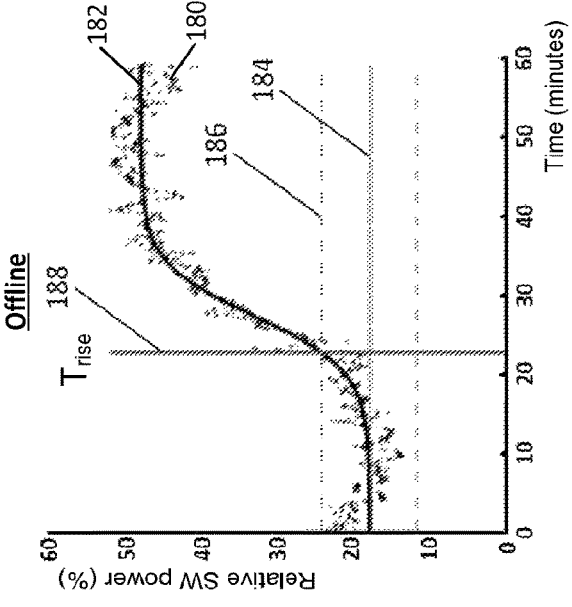
Fig. 22
Fig. 21

PERCEPTION LOSS DETECTION

CROSS REFERENCE TO RELATED APPLICATION

This application is a continuation of U.S. patent application Ser. No. 14/404,337 filed Nov. 6, 2014, which is a National Phase of PCT/GB2013/051446 filed May 30, 2013, which claims priority to U.S. Provisional Patent Application No. 61/746,975 filed Dec. 28, 2012 and GB 1209638.4 filed May 30, 2012, all of which are hereby incorporated by reference herein in their entireties.

BACKGROUND OF THE INVENTION

Technical Field

The invention relates to a device for detecting a state of true perception loss of a human and a related method and computer program product. More particularly, the invention relates to the detection of a neurophysiological marker for a state of true perception loss of a human. The neurophysiological marker is specific to the human and confirms the absence of conscious perception.

SUMMARY OF THE INVENTION

At present there exist inaccurate and indirect methods of measuring this key level of unconsciousness, which do not have a clear scientific basis and are not robust.

There are currently no direct measurements of biological signals that have been shown to detect reliably unconsciousness with perception loss or the return of consciousness with perception gain that is specific for an individual. Current systems rely on indirect measures of cerebral activity, such as coherence between frequencies and are based upon population data. The invention fills this gap but provides also a valuable measure that can not only be exploited by the clinical anaesthesia world but neuroscientific communities as well who want to study this aspect of unconsciousness but to date have not had a biological indicator to time lock analyses and further research around.

Loss of perception can only be reported retrospectively and is currently assumed in the absence of behavioural responses to stimulation or inferred from observation of indirect measures associated probabilistically with subsequent subjective reports of lack of perception. There is currently no measureable physiological process known to preclude perception and no quantification has been shown to be a marker of failed perception.

According to the present invention there is provided a device for detecting a state of true perception loss of a human, the device including processing means operable to detect from information on electrical signals sensed adjacent to (which term, as used herein, preferably connotes for example on, above, or subdural to) the scalp of the human the activity of oscillations (such as those pertaining to physiological activity, notably neural oscillations) present in the electrical signals as a marker for the state of true perception loss of the human. The device may alternatively be suitable for detecting a state of true perception loss of an animal. The detection of true perception loss can enable avoidance of false indication of perception loss, in particular because the detection of physiological changes of the brain function that underlie perception loss is achieved.

Preferably the oscillations are slow wave oscillations and/or alpha oscillations. Preferably the processing means is further operable to detect the saturation of the slow wave oscillations as a marker for the state of true perception loss of the human.

For enhanced functionality, the device may include sensing means operable to sense the electrical signals on (or adjacent to) the scalp of the human. For enhanced functionality, the processing means may be operable to detect a point of saturation of the slow wave oscillations following on a positive gradient of the activity of the slow wave oscillations as a marker for the human entering the state of true perception loss.

For enhanced functionality, the processing means may be operable to detect the onset of a positive gradient of the activity of the slow wave oscillations as a marker for the human starting to lose perception.

For enhanced functionality, the processing means may be operable to detect the onset of a negative gradient of the activity of the slow wave oscillations following on the saturation of the slow wave oscillations as a marker for the human leaving the state of true perception loss.

For reliability, the activity of the slow wave oscillations may be detected by transforming the information to frequency domain information and the activity may be the power of the electrical signals in a slow wave spectral band as a percentage of the power of the electrical signals in a broad spectral band.

The slow wave spectral band may be situated between 0 Hz and 5 Hz, preferably between 0 Hz and 2 Hz, more preferably between 0 Hz and 1.5 Hz and the broad spectral band may include the slow wave spectral band and may be situated between 0 Hz and 50 Hz, preferably between 0 Hz and 30 Hz.

The activity corresponding to the saturation of slow wave oscillations may be between 20 and 100 percent, preferably between 30 and 90 percent, and more preferably between 40 and 80 percent. The activity at saturation may also lie in a narrower range, for example between 45 and 75 percent, or between 50 and 70 percent; or it may lie in a range extending from a different range midpoint, for example between 50 and 90 percent, or between 30 and 70 percent.

The positive gradient may be between 0 and 5 percent of the plateau level, per second. The positive gradient may be dependent on (or affected by) the drug dosage regime or by other parameters, including those relating to the means by which true perception loss is induced, such as physiological factors, e.g. respiratory rate and heart rate, and/or psychological variables.

The negative gradient may be defined with increasing drug dose or other experimental manipulation as between 0 and 5 percent of the plateau level, per second. The negative gradient may be dependent on (or affected by) the drug dosage regime or by other parameters, including those relating to the means by which true perception loss is induced, such as physiological factors, e.g. respiratory rate and heart rate, and/or psychological variables.

For reliability, the activity of the slow wave oscillations may be detected by transforming the information to frequency domain information and the activity may be the power in a slow wave spectral band.

The slow wave spectral band may be situated between 0 Hz and 5 Hz, preferably between 0 Hz and 2 Hz, more preferably between 0 Hz and 1.5 Hz.

For accuracy, the detection of the one or more markers may depend on the maximum activity of the slow wave oscillations of the human.

Preferably the processing means evaluates the detected activity in real time. Preferably the detected activity is evaluated ten times per second, once per second, or once per five seconds.

For accuracy, the processing means may fit the activity of the slow wave oscillations to a model function, and preferably determine (or estimate) best fit parameters. Preferably the model function R in dependence on time t is $$R(t) = a + \frac{b}{1 + \exp(-(t - c)/d)}$$

with a, b, c and d being fit parameters. Preferably the model function R has a normalised model function f(t) in dependence on time t with $$f(t) = \frac{1}{1 + \exp(-(t - c)/d)}.$$

Preferably the best fit parameters are updated with every new activity datapoint (or with every new group of activity datapoints).

Preferably the processing means determines error values associated with the best-fit parameters. Preferably the error value is a confidence interval or a variance estimate for a model function or normalised model function. Preferably error values are updated with every new activity datapoint (or with every new group of activity datapoints).

Preferably the processing means determines a point of saturation and/or an onset of a (positive or negative) gradient by evaluating whether an activity datapoint (preferably the most recent activity datapoint) is within an error range from the model function (or a normalised model function). Preferably the error range is associated with the error value.

The oscillations may include both slow wave oscillations and alpha oscillations. Preferably, the activity of the alpha oscillations is detected by transforming the information to frequency domain information, the activity being the power in an alpha band. Preferably, the alpha spectral band is situated between 7 Hz and 15 Hz, more preferably between 8 Hz and 14 Hz, yet more preferably between 8 Hz and 10 Hz and/or 12 Hz and 14 Hz. Preferably, the processing means is further operable to use the alpha oscillations marker as a marker for the state of true perception loss. Preferably the alpha oscillations marker is related to saturation of alpha oscillations, activity in the alpha spectral band, and/or spindle activity. Saturation of alpha oscillations and activity in the alpha spectral band may be determined analogous to saturation of slow wave oscillations and activity in the slow wave spectral band. Preferably, lower frequency alpha oscillations, which have peak prevalence occurring in advance of a slow wave oscillation saturation point and track the form of slow wave oscillations, and/or higher frequency alpha oscillations, which have peak prevalence in advance of a slow wave oscillation saturation point, but do not track the form of slow wave oscillations, can be used as a further marker for defining saturation.

For accuracy, the detection of the one or more markers may depend on at least one characteristic of the human and in particular the frontal lobe of the human, such as age, sex/gender, volume of grey matter of the frontal lobe of the human, surgical anxiety, trait anxiety, anaesthetic history for the individual, recent sleep deprivation, sleep behaviour, sleep disorders, anatomical connectivity of the brain, for example between brainstem, cortical regions and/or brain lobes, cortical folding and neurotransmitter levels, particularly GABA and Glutamate. A characteristic of the human (and in particular of the human's brain) may be determinable for example by magnetic resonance. The characteristic of the human is preferably related to intra-individual variability of the marker. By considering such a characteristic better prediction of the marker behaviour and better detection of the marker is possible for a given individual. Preferably a weighting is associated with each one of the at least one characteristic of the human.

For configurability, the device may include a database containing parameters defining at least one of the one or more markers more particularly and the parameters may be dependent per marker on at least one of the age, sex/gender, volume of grey matter of the frontal lobe of the human, surgical anxiety history, recent sleep deprivation, sleep behaviour, sleep disorders, anatomical connectivity of the brain (for example the strength of connections between brainstem, cortical regions and/or brain lobes), cortical folding and neurotransmitter levels, particularly GABA and Glutamate, and other measures of the brain that are determinable, for example by magnetic resonance. Preferably a weighting is associated with each one of said factors. The parameters are preferably related to intra-individual variability of the marker. By considering such parameters better prediction of the marker behaviour and better detection of the marker may be possible for a given individual.

For enhanced functionality, the device may include a dose control unit. The dose control unit may be adapted to vary a dose administration output in dependence on a marker for the state of true perception loss. The dose control unit may vary a dose administration output to increase a dose if a marker indicates the absence of the state of true perception loss, and decrease a dose if a marker indicates the presence of the state of true perception loss. The dose control unit may maintain dose administration output dose if a marker indicates the presence of the state of true perception loss. The dose control unit may vary a dose administration output in dependence on a pharmacodynamic and/or pharmacokinetic drug model. The dose control unit may (iteratively) optimise a dose administration output at or above a dose associated with a marker for entering the state of true perception loss. The dose control unit may determine a delay between issuance of a dose administration output and observance of a marker (such as a marker for entering the state of true perception loss, or a delay marker) in response to the dose administration output. The dose administration output may comprise an indicator. The dose administration output may comprise an actuation output for a dose actuation device (such as a valve or a pump).

For enhanced functionality, the processing means may be operable to detect a burst suppression marker as a marker for the state of true perception loss. Preferably, the burst suppression marker is a burst suppression ratio. Preferably, the burst suppression ratio is a fraction of time an oscillation is in a suppressed state (or alternatively brain activity in a suppressed state where multiple oscillations combine to form the observed brain activity). Preferably, in the suppressed state an oscillation has a low amplitude. Preferably, in the suppressed state slow wave oscillations and/or low alpha oscillations have a low amplitude. Preferably, in the suppressed state an oscillation amplitude is in the range of ±10 microvolts, ±5 microvolts, or ±2 microvolts. Preferably, the suppressed state is at least 0.2 second, 0.5 second, or 1 second duration.

For enhanced functionality, the device may include sensing means operable to sense the electrical signals on (or adjacent to) the scalp of the human.

For ease of use, the sensing means may be adapted to be affixed to the scalp of the human. Alternatively, the sensing means may be adapted to be attached subdural to (for example for sensing during brain surgery) or on or above the scalp of the human. Preferably the sensing means is non-invasive.

Preferably the sensing means comprises at least one electrode for sensing the frontal lobe of the human and at least one electrode for sensing the parietal lobe of the human. Preferably the sensing means comprises a plurality of electrodes arranged in a non-uniform distribution over the device with a higher density of electrodes for sensing the frontal lobe of the human. The sensing means may be a band or a headband.

Preferably the device is adapted to detect emergence from a state of true perception loss of a human.

The device may comprise one, some, or all of the following features:
- Means for determining a (time) point of saturation of a slow wave oscillation
- Means for estimating a function describing a time-series of slow wave oscillation data
- Means for establishing a (time) point of interest on the basis of a function describing a time-series of slow wave oscillation data
- Means for feeding back the outcome from analysis of slow wave oscillation data into a system for maintaining a state of true perception loss of a human
- Means for iterative (stair-casing) approximation to optimise maintaining a state of true perception loss of a human
- Means for determining burst suppression as a marker for the state of true perception loss of the human
- Means for maintaining a state of true perception loss of a human, relative to occurrence of saturation of a slow wave oscillation, activity in the alpha band including LFS, HFS, and/or occurrence of burst suppression According to another aspect of the invention, there is provided a method of detecting a state of true perception loss of a human, the method including: providing information on electrical signals sensed adjacent to the scalp of the human; and detecting from the information the activity of oscillations present in the electrical signals as a marker for the state of true perception loss of the human.

Preferably the oscillations are slow wave oscillations and/or alpha oscillations. Preferably the method comprises detecting the saturation of the slow wave oscillations as a marker for the state of true perception loss of the human. Providing the information may include sensing the electrical signals on (or adjacent to) the scalp of the human.

Preferably the method includes detecting a point of saturation of the slow wave oscillations following on a positive gradient of the activity of the slow wave oscillations as a marker for the human entering the state of true perception loss. The method may include detecting the onset of a negative gradient of the activity of the slow wave oscillations following on the saturation of the slow wave oscillations as a marker for the human leaving the state of true perception loss.

The activity of the slow wave oscillations is preferably detected by transforming the information to frequency domain information, the activity being the power of the electrical signals in a slow wave spectral band as a percentage of the power of the electrical signals in a broad spectral band. The slow wave spectral band may be situated between 0 Hz and 5 Hz, preferably between 0 Hz and 1.5 Hz. Preferably the broad spectral band includes the slow wave spectral band and is situated between 0 Hz and 50 Hz, preferably between 0 Hz and 30 Hz.

The activity corresponding to the saturation of slow wave oscillations may be between 20 and 100 percent, preferably between 30 and 90 percent, and more preferably between 40 and 80 percent. The positive gradient may be between 0 and 5 percent of the plateau level, per second. The positive gradient may be dependent on drug dose regime or other parameters relating to the means by which true perception loss is induced. The negative gradient may be between 0 and 5 percent of the plateau level, per second. The negative gradient may be dependent on drug dose regime or other parameters relating to the means by which true perception loss is induced.

Preferably the activity of the slow wave oscillations is detected by transforming the information to frequency domain information, the activity being the power in a slow wave spectral band. The slow wave spectral band is situated between 0 Hz and 5 Hz, preferably between 0 Hz and 1.5 Hz.

Preferably the detection of the one or more markers depends on the maximum activity of the slow wave oscillations of the human.

The oscillations may include both slow wave oscillations and alpha oscillations. The activity of the alpha oscillations may be detected by transforming the information to frequency domain information, the activity being the power in an alpha band.

Preferably the method further comprises using the alpha oscillations marker as a marker for the state of true perception loss.

Preferably the detection of the one or more markers depends on at least one characteristic of the human and in particular the frontal lobe of the human, such as age, sex, volume of grey matter of the frontal lobe of the human, surgical anxiety history, recent sleep deprivation, sleep behaviour, sleep disorders, anatomical connectivity of the brain, cortical folding and neurotransmitter levels. Preferably a weighting each one of the at least one characteristic of the human may be performed. The method may include providing a database containing parameters defining at least one of the one or more markers more particularly, the parameters being dependent per marker on at least one of the age, sex, volume of grey matter of the frontal lobe of the human, surgical anxiety history, recent sleep deprivation, sleep behaviour, sleep disorders, anatomical connectivity of the brain, cortical folding and neurotransmitter levels. Preferably each of said factors are weighted.

Preferably the method includes: providing sensing means operable to be affixed adjacent to the scalp of the human and to sense the electrical signals; providing processing means; and affixing the sensing means adjacent to the scalp of the human; the processing means processing the electrical signals sensed by the sensing means, the processing including detecting the one or more markers. Preferably the sensing means are non-invasive.

According to another aspect of the invention, there is provided a computer program product for detecting a state of true perception loss of a human comprising software code adapted, when executed on a data processing apparatus, to perform the step of detecting from information on electrical signals sensed adjacent to the scalp of the human the activity of oscillations present in the electrical signals as a marker for the state of true perception loss of the human.

Preferably the oscillations are slow wave oscillations and/or alpha oscillations. The computer program product may be adapted to perform the step of detecting the saturation of the slow wave oscillations as a marker for the state of true perception loss of the human. The computer program product may be adapted to perform the step of detecting a point of saturation of the slow wave oscillations following on a positive gradient of the activity of the slow wave oscillations as a marker for the human entering the state of true perception loss. Preferably the computer program product is adapted to perform the step of detecting the onset of a negative gradient of the activity of the slow wave oscillations following on the saturation of the slow wave oscillations as a marker for the human leaving the state of true perception loss.

Preferably the activity of the slow wave oscillations is detected by transforming the information to frequency domain information, the activity being the power of the electrical signals in a slow wave spectral band as a percentage of the power of the electrical signals in a broad spectral band. The slow wave spectral band may be situated between 0 Hz and 5 Hz, preferably between 0 Hz and 1.5 Hz and wherein the broad spectral band includes the slow wave spectral band and is situated between 0 Hz and 50 Hz, preferably between 0 Hz and 30 Hz. The activity corresponding to the saturation of slow wave oscillations may be between 20 and 100 percent, preferably between 30 and 90 percent, and more preferably between 40 and 80 percent. The positive gradient may be between 0 and 5 percent of the plateau level, per second. Preferably the positive gradient is dependent on drug dose regime or other parameters relating to the means by which true perception loss is induced. The negative gradient may be between 0 and 5 percent of the plateau level, per second. Preferably the negative gradient is dependent on drug dose regime or other parameters relating to the means by which true perception loss is induced.

Preferably the activity of the slow wave oscillations is detected by transforming the information to frequency domain information, the activity being the power in a slow wave spectral band. The slow wave spectral band may be situated between 0 Hz and 5 Hz, preferably between 0 Hz and 1.5 Hz.

Preferably the detection of the one or more markers depends on the maximum activity of the slow wave oscillations of the human.

Preferably the oscillations include both slow wave oscillations and alpha oscillations. The activity of the alpha oscillations may be detected by transforming the information to frequency domain information, the activity being the power in an alpha band. The computer program product may further be adapted to perform the step of using the alpha oscillations marker as a marker for the state of true perception loss.

Preferably the detection of the one or more markers depends on at least one characteristic of the human and in particular the frontal lobe of the human, such as age, sex, volume of grey matter of the frontal lobe of the human, surgical anxiety history, recent sleep deprivation, sleep behaviour, sleep disorders, anatomical connectivity of the brain, cortical folding and neurotransmitter levels. Preferably, a weighting is associated with each one of the at least one characteristic of the human. The computer program product may include a database in which parameters defining at least one of the one or more markers more particularly can be stored, the parameters being dependent per marker on at least one of the age, sex, and volume of grey matter of the frontal lobe of the human. Preferably, a weighting is associated with each said factor.

According to another aspect of the invention, there is provided a device for detecting a state of true perception loss of a human, the device including sensing means operable to sense the electrical signals on (or adjacent to) the scalp of the human, the sensing means comprising at least one electrode for sensing the frontal lobe of the human and at least one electrode for sensing the parietal lobe of the human.

Preferably the sensing means comprises a plurality of electrodes arranged in a non-uniform distribution over the device with a higher density of electrodes for sensing the frontal lobe of the human. The sensing means may be a band or a headband.

The invention extends to any novel aspects or features described and/or illustrated herein.

Further features of the invention are characterised by the other independent and dependent claims.

The invention extends to methods and/or apparatus substantially as herein described with reference to the accompanying drawings.

Any apparatus feature as described herein may also be provided as a method feature, and vice versa. As used herein, means plus function features may be expressed alternatively in terms of their corresponding structure, such as a suitably programmed processor and associated memory.

Any feature in one aspect of the invention may be applied to other aspects of the invention, in any appropriate combination. In particular, method aspects may be applied to apparatus aspects, and vice versa. Furthermore, any, some and/or all features disclosed in the description, and (where appropriate) the claims and drawings in one aspect can be applied to any, some and/or all features in any other aspect, in any appropriate combination.

It should also be appreciated that particular combinations of the various features described and defined in any aspects of the invention can be implemented and/or supplied and/or used independently.

The invention also provides a computer program and a computer program product comprising software code adapted, when executed on a data processing apparatus, to perform any of the methods described herein, including any or all of their component steps.

The invention also provides a computer program and a computer program product comprising software code which, when executed on a data processing apparatus, comprises any of the apparatus features described herein.

The invention also provides a computer program and a computer program product having an operating system which supports a computer program for carrying out any of the methods described herein and/or for embodying any of the apparatus features described herein.

The invention also provides a computer readable medium having stored thereon the computer program as aforesaid.

The invention also provides a signal carrying the computer program as aforesaid, and a method of transmitting such a signal.

Furthermore, features implemented in hardware may be implemented in software, and vice versa. Any reference to software and hardware features herein should be construed accordingly.

Each feature disclosed in the description, and (where appropriate) the claims and drawings may be provided independently or in any appropriate combination.

BRIEF DESCRIPTION OF THE DRAWINGS

The present invention will now be described, purely by way of example, with reference to the accompanying diagrammatic drawings, in which:

FIG. 18 shows slow wave data with a best fit curve and associated error values for estimating the onset of a gradient in slow wave data;

FIG. 19 shows normalised slow wave data with a best fit normalised curve and associated error values for estimating the point at which slow wave data displays saturation;

FIG. 21 shows a comparison of the curve fits and estimate for online and offline data analysis for estimating the onset of a gradient in slow wave data;

FIG. 22 shows a comparison of the curve fits and estimate for online and offline data analysis for estimating the point at which slow wave data displays saturation;

With reference to FIGS. 1 to 3 of the drawings, a method of detecting a neurophysiological marker for a state of true perception loss of a human is designated, generally, by the reference numeral 10. The method in the illustrated example is executed concurrently with the administration of an anaesthetic agent in the form of propofol to the human 12.

The method is executed using a slow wave activity maximum plateau (SWAMP) system (hereinafter "SWAMP", also referred to as slow wave activity saturation "SWAS") 14 which includes sensing means in the form of multiple electrodes 16, processing means in the form of a processor 18 and a database 19.

The multiple electrodes 16 are affixed to the scalp of the human 12. Electrical signals in the form of voltage fluctuations detected by the electrodes are relayed to the processor 18 for processing.

Figure 1:
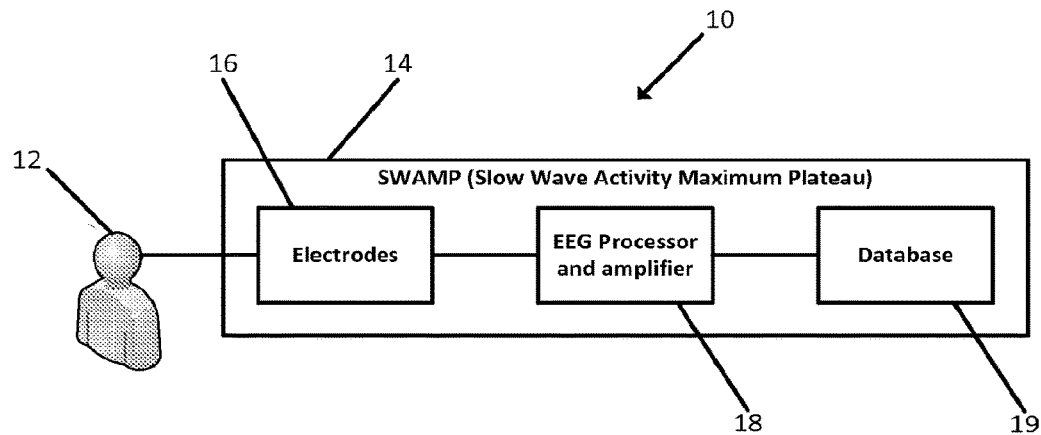
FIG. 1 shows a schematic view of a method of detecting a state of true perception loss of a human in accordance with the invention.
Figure 2:
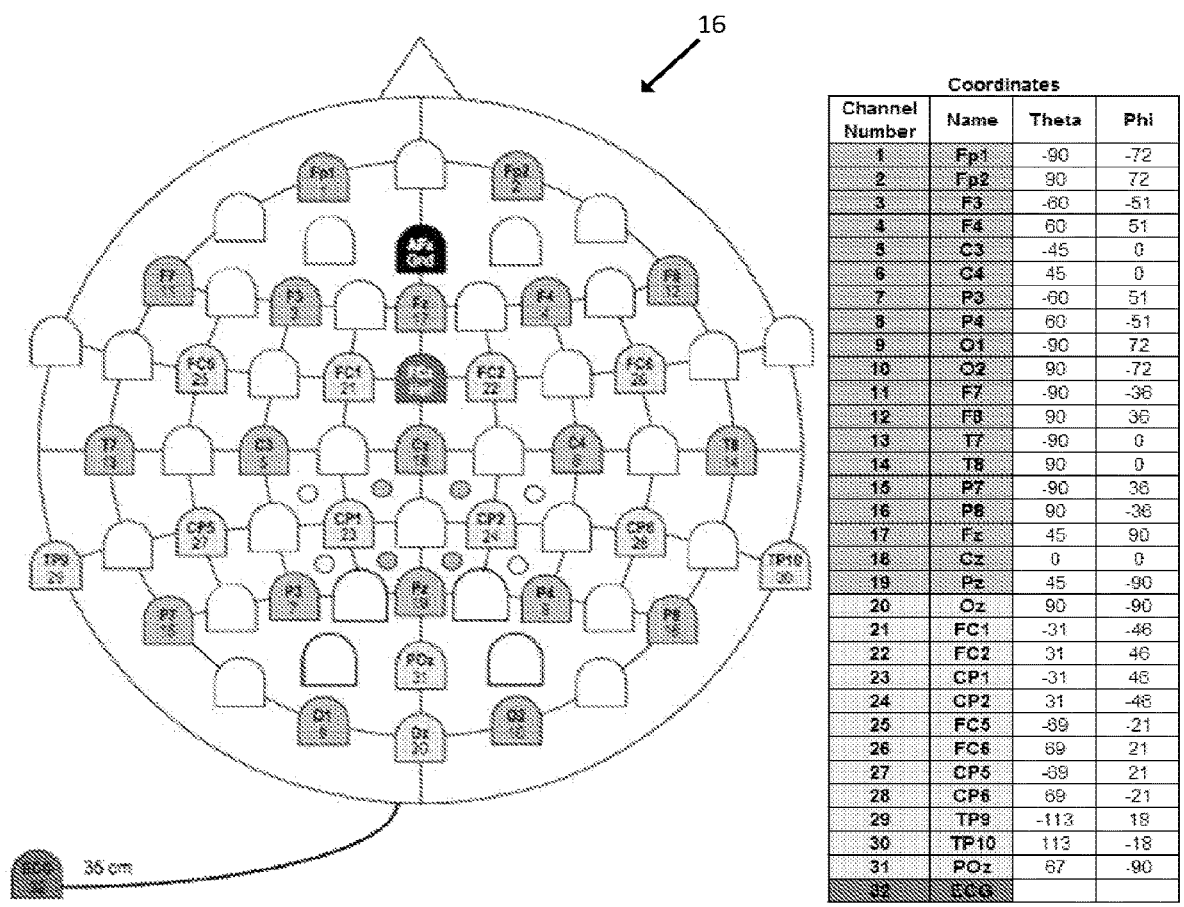
FIG. 2 shows a schematic view of a montage of electrodes together with exemplary electrode co-ordinates used in the method of FIG. 1.
Figure 3:
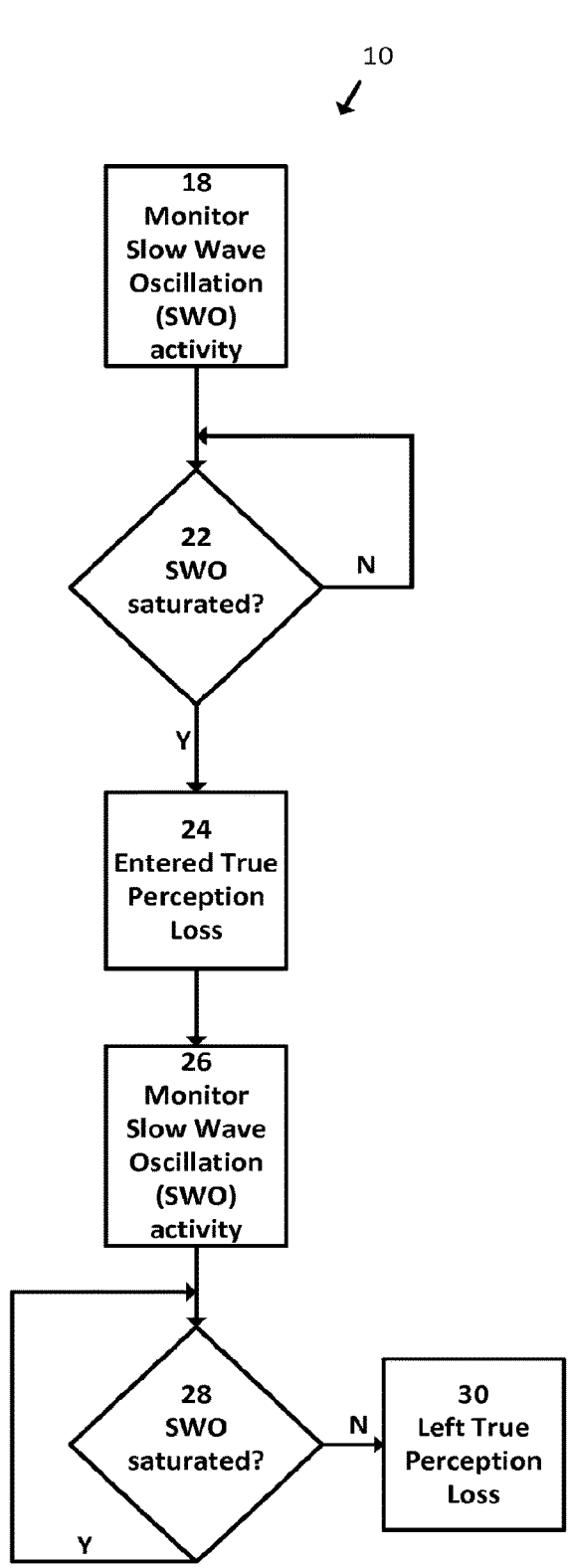
FIG. 3 shows a flowchart describing the steps of the method of FIG. 1.

Multiple electrodes, including Magnetic Resonance (hereinafter "MR") compatible 32 channel electroencephalography (hereinafter "EEG") caps (BrainCap MR, Easycap GmbH, Herrsching, Germany) are used in the illustrated example for EEG acquisition. The schematic of the montage used with electrode co-ordinates shown in FIG. 2 is based on the standard international 10-20 arrangement of electrodes. In some circumstances not necessarily all of the electrodes shown in FIG. 2 might be employed; for example, only a subset, such as only frontal electrodes, can be used for EEG acquisition.

Inbuilt electrodes 16 are in the illustrated example in the form of sintered Ag/AgCl sensors with 5 kOhm resistors directly after the sensor except the electrocardiogram (hereinafter "ECG") electrode which has a 15 kOhm resistor. To reduce impedance before placement of electrodes, the skin under the electrodes is cleaned with isopropyl alcohol, and a conducting electrolyte gel is applied to fill any gaps between the electrodes and the skin. Impedances are ideally kept below 5 kilohms throughout all experiments.

For MR data acquisition, cables from the EEG electrodes 16 are twisted into branches of 8 cables that are brought together to unite into a single 50 cm twisted cable tree. This cable tree is connected to two 16 channel MR compatible biopotential amplifiers (BrainAmp MR plus, Brain Products GmbH, Munich, Germany). Additional channels are connected through an auxiliary device and record electrocardiography (ECG), vertical eye movements and horizontal eye movements. When being used in a functional Magnetic Resonance Imaging (hereinafter "fMRI") scanner any loops in the cabling are eliminated.

Amplifiers are connected in the illustrated example using MR-safe fibre optic cables to a universal serial bus (USB) adaptor and then to a laptop computer (or other recording and EEG processing medium), which includes the processor 18 and the database 19. The laptop simultaneously records the timings of fMRI volumes (gradient onset markers), stimuli and button presses. For the paradigm in FIG. 5, samples of the electrical signals are acquired at 5000 Hz and initially referenced to channel CPz. The amplification hardware imposes a highpass filter of 0.1 Hz and a lowpass filter of 250 Hz on acquisition. The acquisition software applies a highpass filter of 0.5 Hz and a lowpass filter of 70 Hz as well as a notch filter of 50 Hz. The lower frequency limit of the data obtained from the instrumentation described above is 0.5 Hz; however with different instrumentation data can be acquired down to yet lower limits.

The database 19 contains parameters of the neurophysiological markers which are detected by the SWAMP system. Each marker has particular characteristics which are parameterised in terms of the parameters. So, for example, a characteristic can be a gradient of relative power of slow wave oscillations and a corresponding parameter can be a range of gradient of relative power values. The parameters are dependent per marker on at least one of the age, sex, surgical anxiety, trait anxiety, volume of grey matter of the frontal lobe of the human, recent sleep deprivation, sleep behaviour, sleep disorders, anatomical connectivity of the brain, for example between brainstem, cortical regions and/or brain lobes, cortical folding, neurotransmitter levels, particularly GABA and Glutamate and other measures of the brain. Such measures can for example be determinable for a subject by magnetic resonance in advance of the induction of perception loss. These parameters can be used to address intra-individual variability of the slow wave and/or alpha oscillations. By considering such parameters better prediction of the marker behaviour and better detection of the marker is possible for a given individual. The parameters can have weightings associated with them.

For example if the influence of subject age is dominant, then the age weighting is high relative to the weightings of other parameters. The weightings can also depend on the actual parameter values, for example if the subject age is over 70 then it is a dominant parameter with a high weighting; or if the subject age is over 70 then the weighting of the parameter relating to the volume of grey matter of the frontal lobe of the human is lower than otherwise.

The processor 18 processes the samples of the electrical signals detected by the electrodes 16.

Generally, the processor 18 monitors (Block 18) the activity of slow wave oscillations. The samples of the electrical signals are transformed into frequency domain information. The activity of the slow wave oscillations is determined as the power of the electrical signals in a slow wave spectral band as a percentage of the power of the electrical signals in a broad spectral band. The slow wave spectral band is assumed to extend from 0 Hz to 1.5 Hz in the illustrated example. The broad spectral band includes the slow wave spectral band and extends from 0 Hz to 30 Hz. The slow wave oscillations activity at saturation is between 40 and 80 percent.

The processor detects the saturation (Block 22) of the slow wave oscillations. On such detection, the (time) point of saturation is identified (Block 24) as a marker for the human entering the state of true perception loss. Prior to saturation, the slow wave oscillations increase with increasing anaesthetic dose. At saturation, the slow wave oscillations cease to increase with increasing anaesthetic agent dose. Saturation is characterised by the loss of dose dependency of the slow wave oscillations.

The processor continues to monitor (Block 26) the activity of the slow wave oscillations and detects (Block 28) the slow wave oscillations becoming unsaturated. On such detection, the point at which the slow wave oscillations become unsaturated is identified (Block 30) as a marker for the human leaving the state of true perception loss.

Parameters dependent on the age, sex, surgical anxiety, trait anxiety, volume of grey matter of the frontal lobe of the human, recent sleep deprivation, sleep behaviour, sleep disorders (and other factors) are queried from the database 19 to assist with the detection of the marker. The values of the parameters are generally dependent on the maximum power of the slow wave oscillations on the scalp of the human. The parameters include a range of values for the level of saturation per combination of age, sex, surgical anxiety, trait anxiety, volume of grey matter of the frontal lobe of the human, recent sleep deprivation, sleep behaviour and sleep disorders.

More specifically, the saturation point of the slow wave oscillations is a neurophysiological marker for the time-point at which the brain cannot process information from the outside world, rendering a human unconscious and with loss of perception.

During propofol anaesthesia (a commonly used anaesthetic agent) the activity of slow wave oscillations in the scalp electroencephalogram reaches a maximum or saturation point after the human has lost verbal responsiveness and subsequent to increasing doses of propofol.

When drugs are given to suppress consciousness, a sleep-like state is imposed upon the brain, and the nerve cells of the brain show membrane fluctuations. The voltage across the cell membrane oscillates from ON to OFF states and the oscillation is maintained by a balance of sleep-wake drivers in the brain. The more nerve cells engaged in this oscillation, the higher the measured activity in the slow wave frequency band (approximately 0 to 1.5 Hz) at the scalp. The activity rises until the maximum number of nerve cells behaves this way, and slow wave activity is in effect saturated. Further increases in drug levels do not increase the activity level within the slow wave frequency band.

With reference to FIGS. 5 to 11 of the drawings, during an experiment conducted using EEG, 16 subjects were induced into a state of true perception loss through the gradual administration of propofol. The subjects were thereafter allowed to recover. Throughout the experiment the subjects were subjected to sensory stimuli in order to elicit neural responses. The duration of the experiment was 116 minutes.

Figure 5:
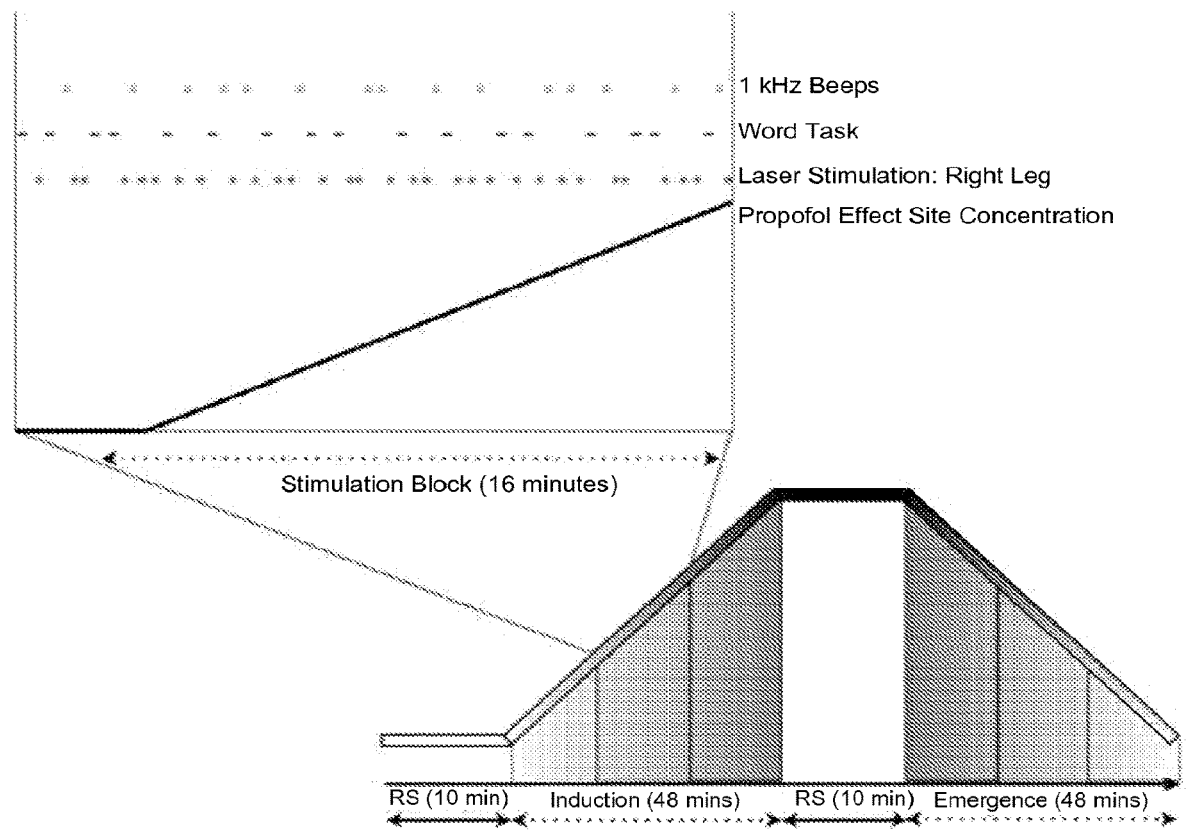
FIG. 5 shows a schematic view of the paradigm and an example propofol induction regime for an experiment conducted in accordance with the method of FIG. 1.

With reference to FIG. 5, a schematic of the paradigm of the experiment and the propofol induction regime is presented. Each block of stimulation was sixteen minutes long and was accompanied by a sequence of inter-leaved laser stimuli, computer generated tones and cognitive word tasks. Three contiguous stimulation blocks were delivered during both the induction and recovery phases. Furthermore, two 10 minute resting state (RS) periods were included at the start of the experiment (RS-awake) and at the peak propofol dose (RS-peak), resulting in total data collection time of approximately two hours. No stimuli were delivered during the RS periods. During the RS-awake period, subjects were asked to remain still with their eyes closed to match the expected behaviour during the RS-peak period.

Figure 6:
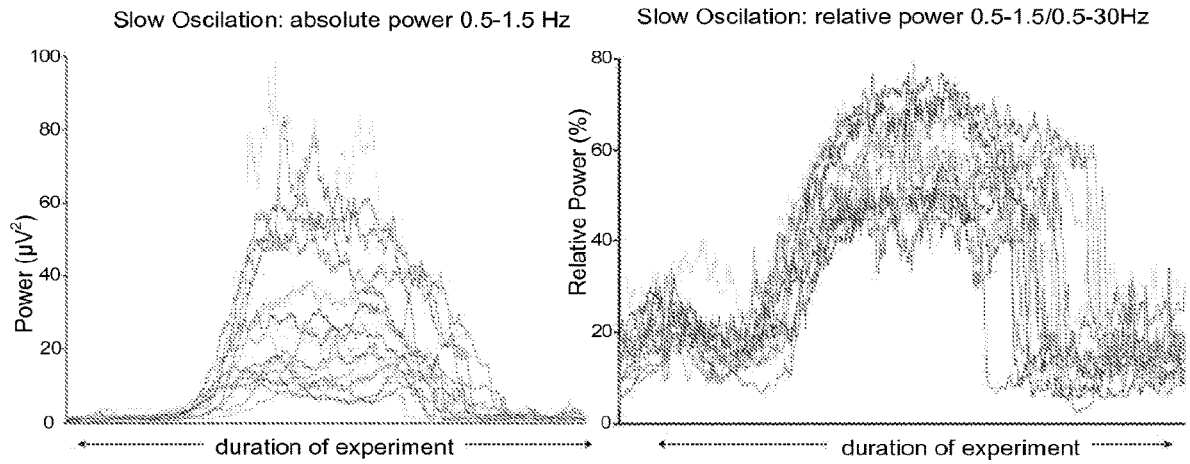
FIG. 6 shows a plot of absolute power in the 0.5-1.5 Hz frequency band data together with a plot of relative power in the 0.5-1.5 Hz frequency band data obtained from subjects who participated in the experiment of FIG. 5.

With reference to FIG. 6, in the plot on the left absolute power of slow wave oscillations shows the same pattern for each subject although there is marked variability between subjects in peak power (range 10.84-83.78 µV2). In the plot to the right, power as a percentage of the total power in the 0.5-30 Hz band is shown.

Figure 7:
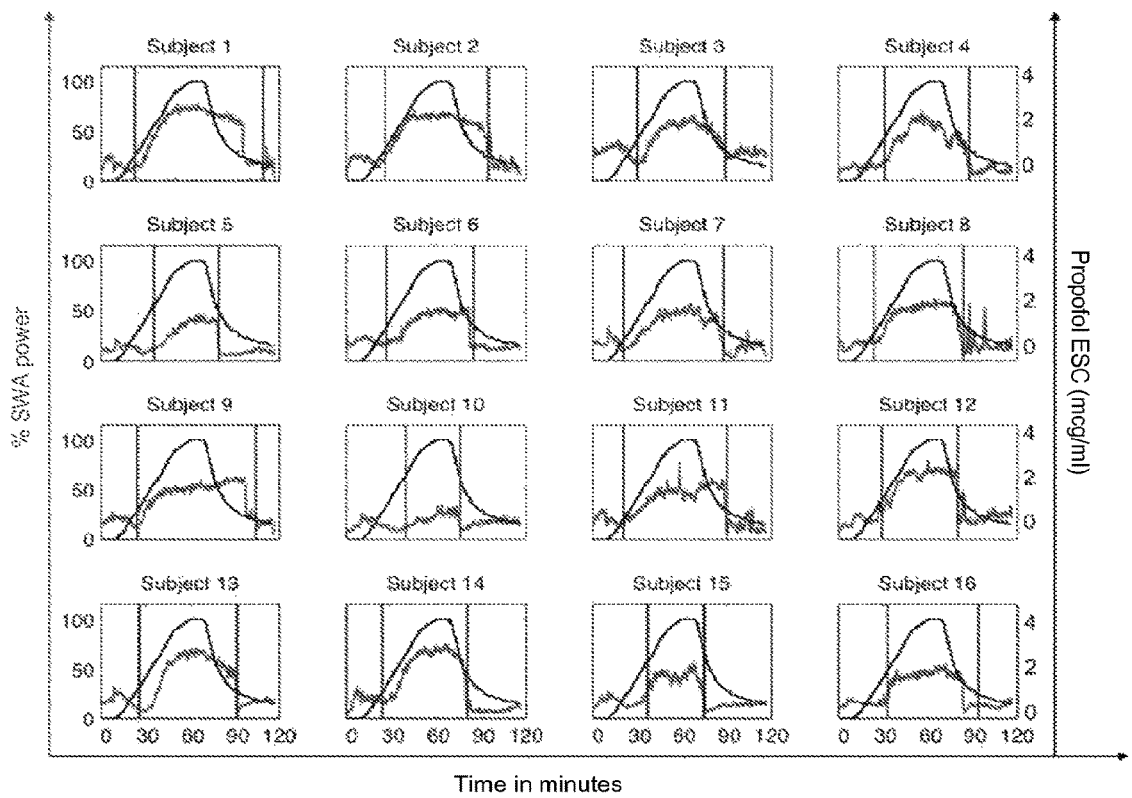
FIG. 7 shows a separate plot of relative power of oscillations in the 0.5-1.5 Hz frequency band superimposed on propofol effect site concentration during the experiment of FIG. 5 for each of the subjects.

With reference to FIG. 7, a consistent pattern of relative slow wave oscillation power is evident for each of the subjects of the experiment. For each subject, slow wave oscillation power rises rapidly after which it reaches a plateau at which it remains until dropping off sharply during recovery.

Figure 8:
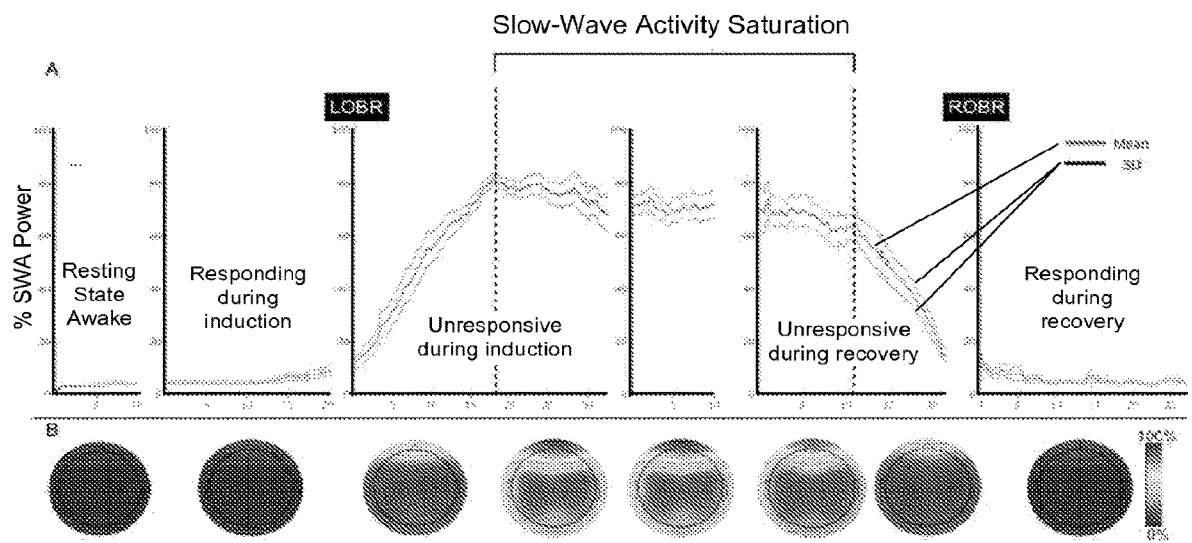
FIG. 8 shows a plot of the mean and standard deviation of relative slow wave oscillation power together with topographic brain representations in plan view of the mean relative slow wave oscillations power during a number of behavioural phases for the subjects of and during the experiment of FIG. 5.

With reference to FIG. 8, the mean (appearing as the darker line) and standard deviation (appearing as the lighter lines) of relative slow wave oscillations power during a number of behavioural phases for the subjects of and during the experiment are shown. In the top section of FIG. 8, the plot is divided in accordance with the phases of the experiment. The phases being a resting state awake phase, a responding during induction phase which includes early responsive and late responsive (with increased beta activity and psychomotor retardation) sub phases, an unresponsive during induction phase with slow wave oscillations power rising and slow wave oscillations saturation sub phases, a resting state phase at a peak propofol level of 4.0 mcg ml−1, an unresponsive during recovery phase with slow wave oscillations saturation and slow oscillations power falling sub phases and a responding during recovery phase including early recovery and late recovery sub phases. The point of the last response among the subjects during the late responsive phase is indicated by 'LOBR' and the point of the first response among the subjects during the early recovery phase is indicated by 'ROBR'.

Following loss of behavioural response, slow wave oscillation power continues to rise until it reaches saturation, after which point it remains at a plateau (with a slight decrease due to burst suppression in those subjects in whom burst suppression developed) until after the administration of propofol is discontinued. Relative slow wave oscillation power decreases sharply prior to return of behavioural response.

Given that when slow wave oscillation power is at a plateau and a slight decrease due to burst suppression can occur (in those subjects in whom burst suppression develops), an algorithm can be implemented to distinguish a decrease due to burst suppression from a decrease due to regain of perception. For example, the percentage of time spent in slow wave oscillation can be referred to, or a suitable tolerance level for identifying a decrease as the onset of regain of perception can be defined.

Topographic representations of mean relative slow wave oscillation power (blue 0%-red 100%) in the brain are shown in the bottom section of FIG. 8 for the subjects of and during the experiment. The highest slow wave oscillation power is frontal, consistent with the fact that slow wave oscillation peak power is correlated with grey matter volume in the frontal lobe but not in other cortical regions.

Figure 10:
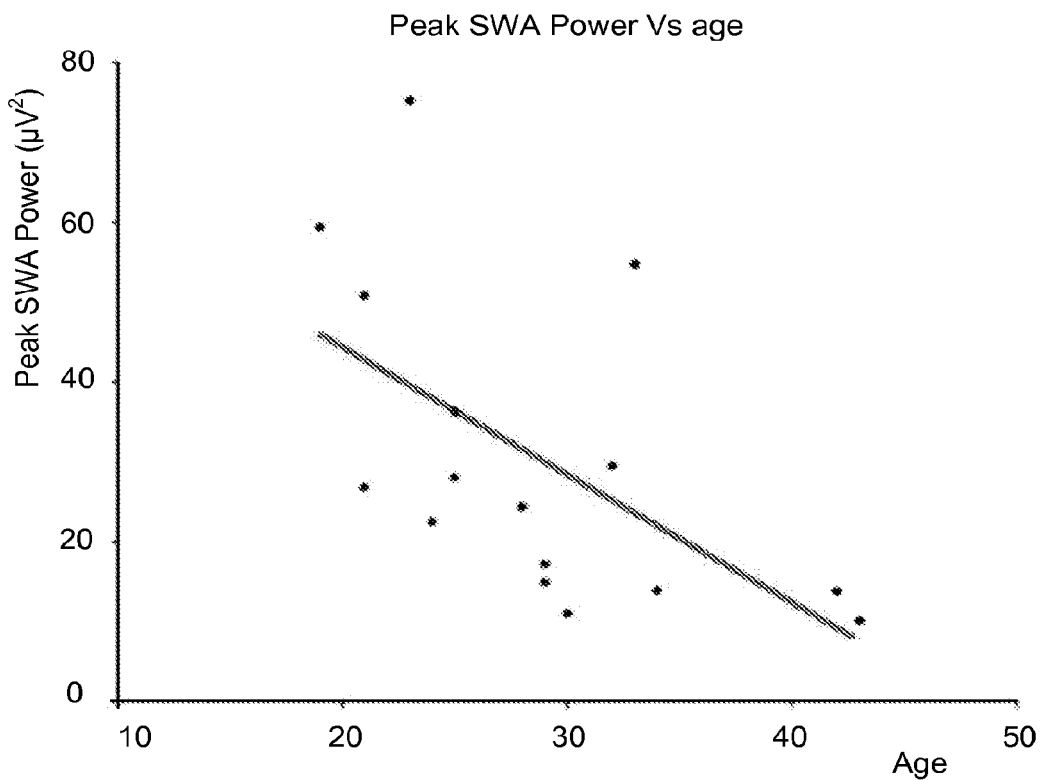
FIG. 10 shows a plot of the peak power of slow wave oscillations versus age for the subjects of and during the experiment of FIG. 5.

With reference to FIG. 10 of the drawings, the peak power of slow wave oscillation activity was negatively correlated with subject age.

Figure 11:
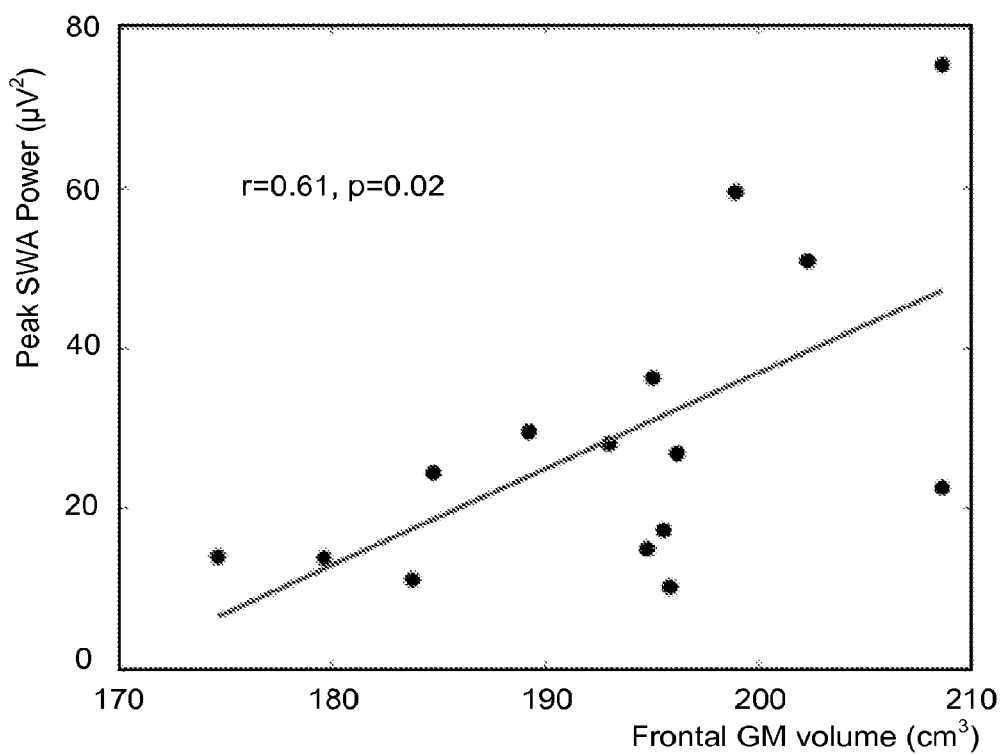
FIG. 11 shows a plot of the peak slow wave oscillations power versus frontal grey matter volume for the subjects of and during the experiment of FIG. 5.

With reference to FIG. 11 of the drawings, the peak relative slow wave oscillations power was positively correlated with subject frontal grey matter volume only (p=0.02 corrected), which declines with age. Voxel-Based Morphometry (VBM) was used to estimate the grey matter volume in the frontal, temporal, insular, parietal and occipital lobes, the hypothesis being that the number of neurons available to participate in slow wave oscillations would influence the amplitude of activity that could be generated.

The effect of age on peak slow wave oscillation power may therefore be a function of age related changes in frontal grey matter volume. Alternatively, slow wave oscillation peak power may equally be a function of the strength of synaptic connections facilitating slow wave oscillation synchrony, which may also vary with age.

Figure 12:
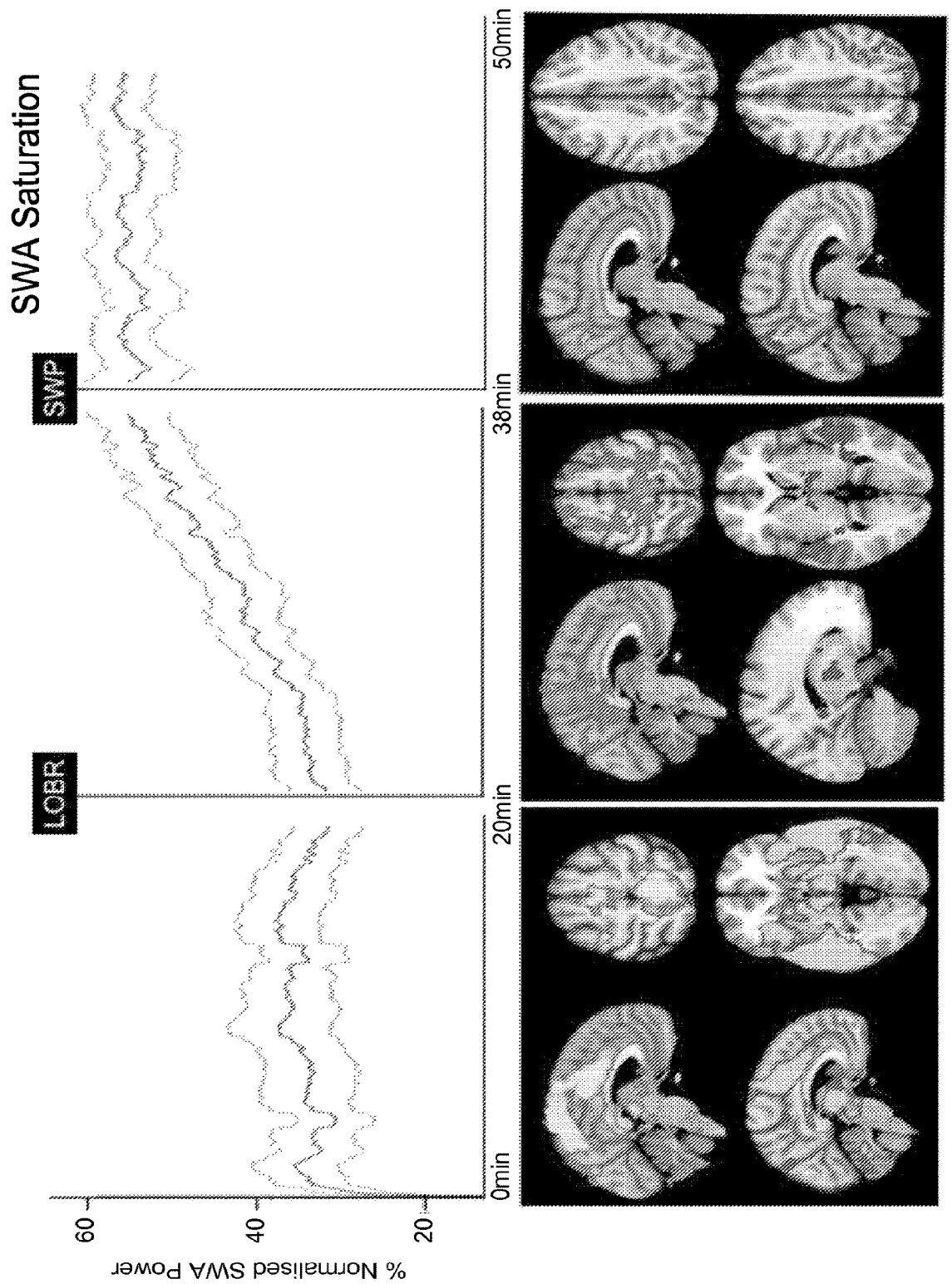
FIG. 12 shows a plot of group mean percentage normalised power of slow wave oscillations in the 0.5-1.5 Hz frequency band together with group mean functional magnetic resonance imaging (fMRI) Blood Oxygen Level Dependent ("BOLD") responses before loss of behavioural response, between loss of behavioural response and slow wave oscillations saturation, and during slow wave oscillations saturation for subjects who participated in another experiment in accordance with the method of FIG. 1.
Figure 13:
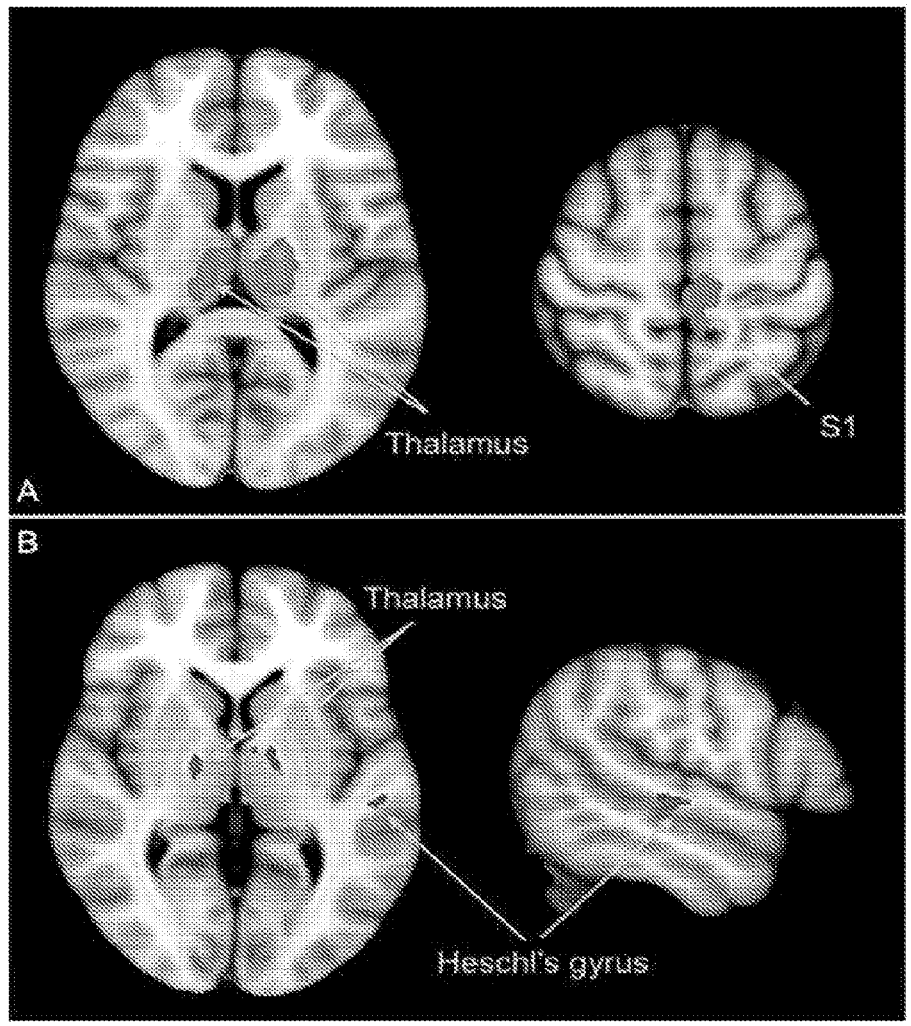
FIG. 13 shows fMRI BOLD responses, indicating the change in activation in response to laser (top BOLD response) and auditory stimuli (bottom BOLD response) across the transition to slow wave oscillations saturation.

With reference to FIG. 12 and FIG. 13 of the drawings, in a second experiment, twelve of the original sixteen subjects completed a 48-minute ultraslow sedation protocol identical to that of the first experiment in an fMRI scanner while simultaneous EEG and fMRI data were collected. As was observed during the bench EEG session of the first experiment, slow wave oscillations saturation occurring after Loss Of Behavioural Response (hereinafter "LOBR") and while propofol concentrations were still rising is evident in the top section of FIG. 12. Group mean fMRI Blood Oxygen Level Dependent (hereinafter "BOLD") responses are divided for analysis into three temporal regions of interest—before LOBR, between LOBR and slow wave oscillations saturation, and during slow wave oscillations saturation in the bottom section of FIG. 12.

While the behavioural transition (LOBR) was associated with a significant reduction in activation in several cortical areas relevant to auditory and nociceptive inputs (e.g. secondary somatosensory cortex, insula, cingulate cortex) significant activity persisted in the thalamus and primary cortical processing regions of the now unresponsive subjects (FIG. 12, middle figure). Rather, it was the EEG transition to slow wave oscillation saturation that was specifically associated with loss of thalamic and primary cortical activation, as determined using fMRI (FIG. 12, right hand figure).

Figure 9:
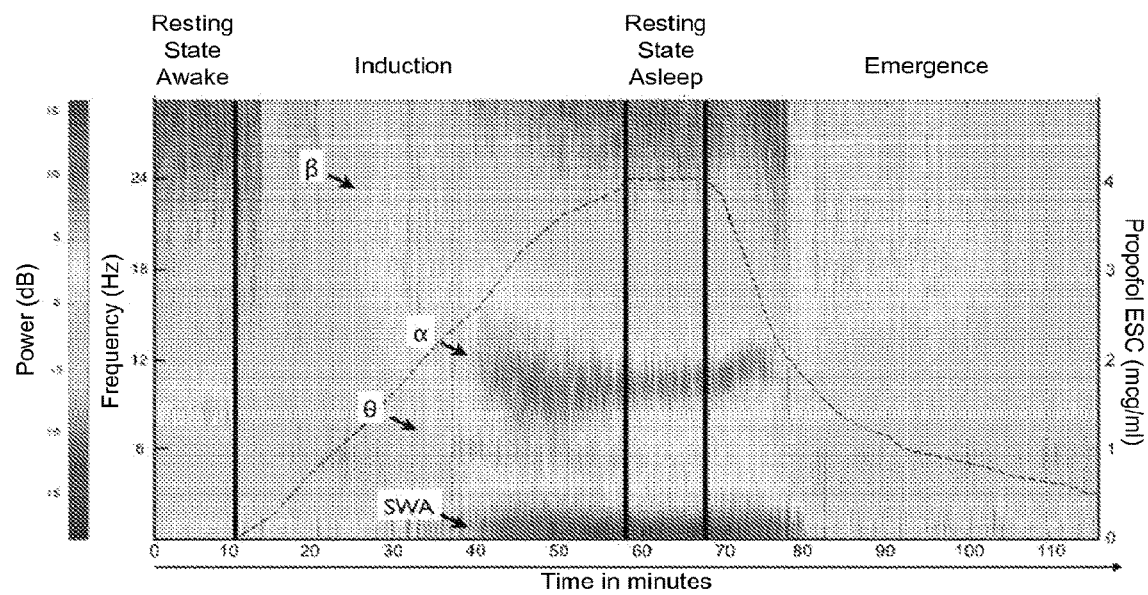
FIG. 9 shows propofol effect site concentration of the experiment of FIG. 5 superimposed on a plot of the group mean power of brain wave oscillations over a spectrum of frequencies for the subjects of and during the experiment of FIG. 5.

The ON state of the slow oscillation coincides with spindle activity. Reverberations (oscillations) of thalamo-cortical neurons at alpha band frequencies are referred to as spindles. The alpha band frequency is between 8 and 14 Hz. With reference to FIG. 9, the persistence of activity in alpha band frequencies at the same time as slow wave oscillation saturation shows that failure of perception, as indicated by the fMRI data, is unlikely to be explained by a "thalamo-cortical switch", as clearly thalamocortical dialogue exists.

Figure 14:
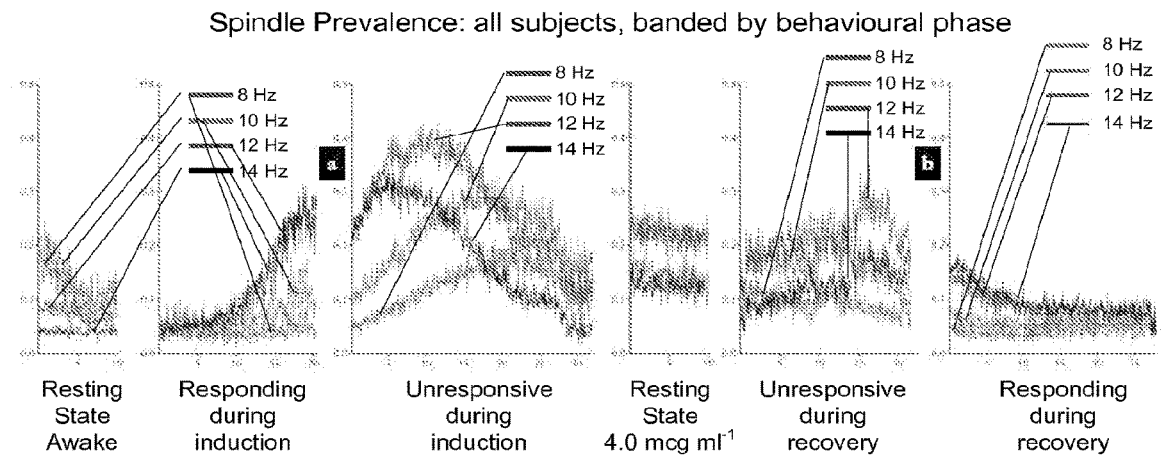
FIG. 14 shows the prevalence of spindles in the alpha frequency band (8-14 Hz) across the behavioural phases for the subjects of and during the experiment of FIG. 5.

With reference to FIG. 14, the persistence of spindle activity after LOBR is specific to certain frequencies within the alpha band. Low Frequency Spindles (LFS, 8-10 Hz, shown lightest) increase in prevalence during the late unresponsive phase. Particularly, 10 Hz spindles accompany SWAMP or even slightly precede saturation. Higher Frequency Spindles (HFS, 12-14 Hz, shown darkest) precede LOBR and reach peak prevalence earlier in the unresponsive phase.

Figure 15:
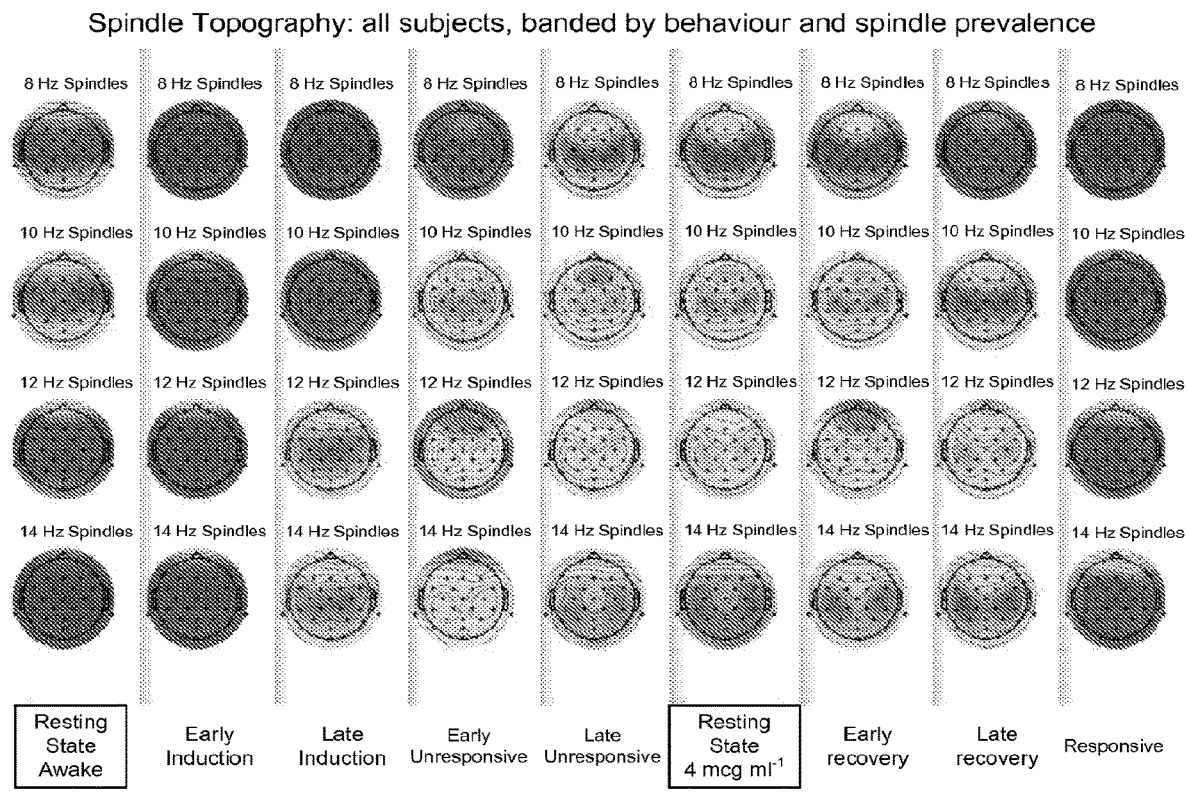
FIG. 15 shows the topographical distribution of spindle oscillations in the alpha frequency band (8-14 Hz) across the behavioural phases for the subjects of and during the experiment of FIG. 5.

With reference to FIG. 15, the topographic distinction of the LFS (blue 0%-red 100%) is demonstrated to be largely frontal in topography during the late unresponsive period in-line with previous topography of the slow wave oscillations in FIG. 8.

Figure 16:
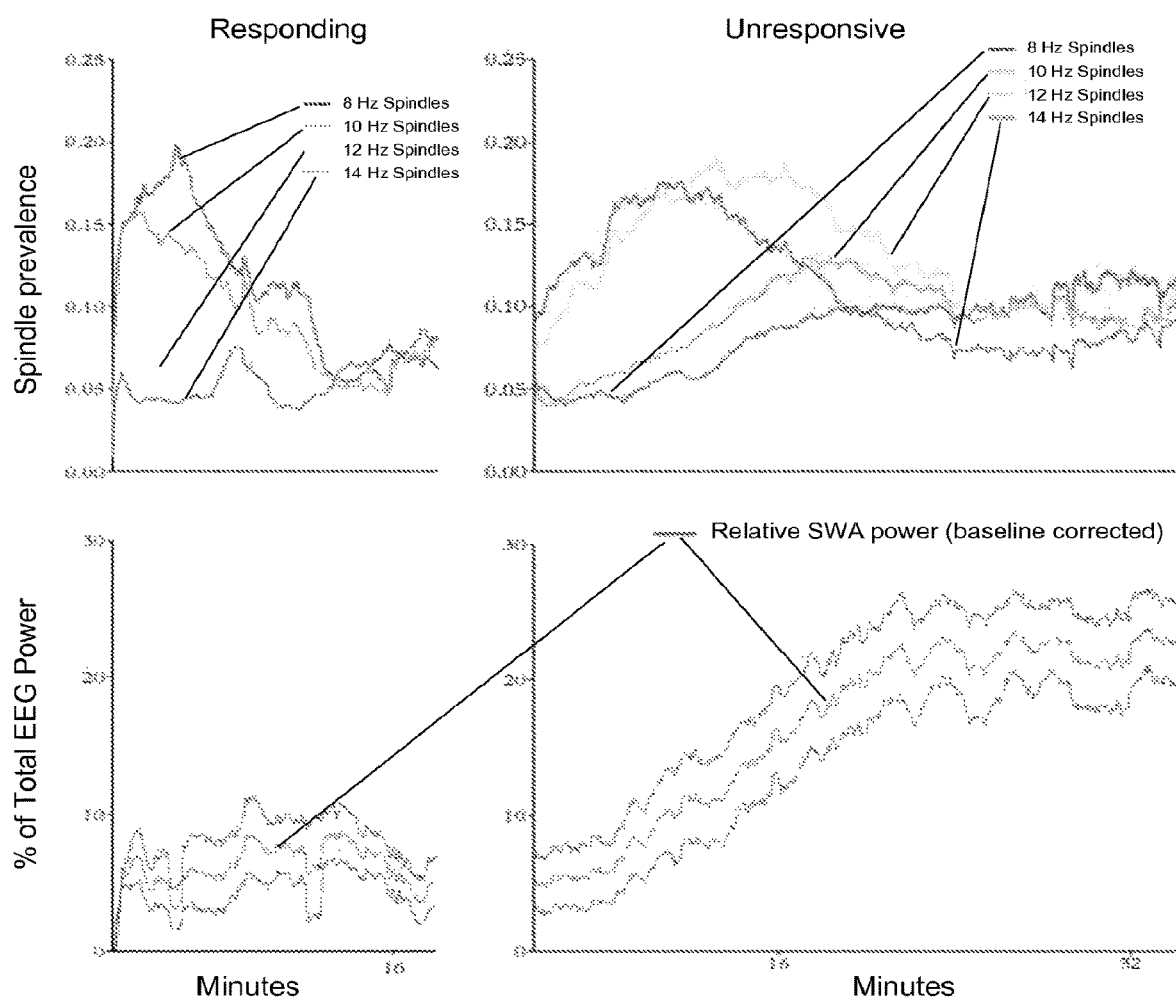
FIG. 16 shows a comparison of slow wave oscillations and spindle activity during the FMRI experiment performed in accordance with the method of FIG. 1 during the responsive and unresponsive behavioural phases.

With reference to FIG. 16, the comparison of the temporal dynamics of the slow wave oscillations and LFS show distinct similarities. The peak prevalence of the LFS occurs in advance of slow wave oscillation saturation point and can track the form of the rise and plateau of slow wave oscillations in the unresponsive phase; as such LFS can be used as a further marker for defining saturation. HFS (12 Hz shown lightest) have peak prevalence in advance of slow wave oscillation saturation point, but do not track the form of the slow wave oscillations, can be used in addition to or independent of LFS as a marker for defining saturation.

With reference to FIG. 13, support for this thalamocortical deafferentation is provided by the mixed effects mean group subtraction results for pre-slow wave oscillation saturation and slow wave oscillations saturation during the LOBR period for laser (top figure) and auditory stimulation (bottom figure). Therefore, slow wave oscillations saturation is when functional deafferentation and true loss of perception occurs.

Supporting that the brain was neither inactive nor unresponsive beyond thalamocortical isolation, both auditory and noxious stimulation were associated with specific BOLD signal changes. This activation was not within the sensory thalamocortical system but involved a network of precuneus, posterior parietal and prefrontal cortices. Important recent functional imaging studies in patients with altered states of consciousness have reported that activity within this network is the first to show an increase in metabolism and blood flow in parallel with recovery. The precuneus has rich reciprocal connections to posterior parietal, retrosplenial and prefrontal cortical areas but does not project directly to primary somatosensory cortices, brainstem nuclei or the relay or association thalamic nuclei. It does however have connections with the midline and intralaminar thalamic nuclei, which play a key role in the regulation of consciousness. The experimental results suggest activity within this network reflects a capacity for arousal when the thalamocortical network has been pharmacologically rendered refractory to external inputs.

In summary, the experimental results show that upon saturation of slow wave oscillations thalamocortical isolation occurs from external sensory inputs. This neurophysiologically defined transition is a potential and much sought-after biomarker of an anaesthetised state where lack of perceptual awareness to sensory events occurs.

Figure 4:
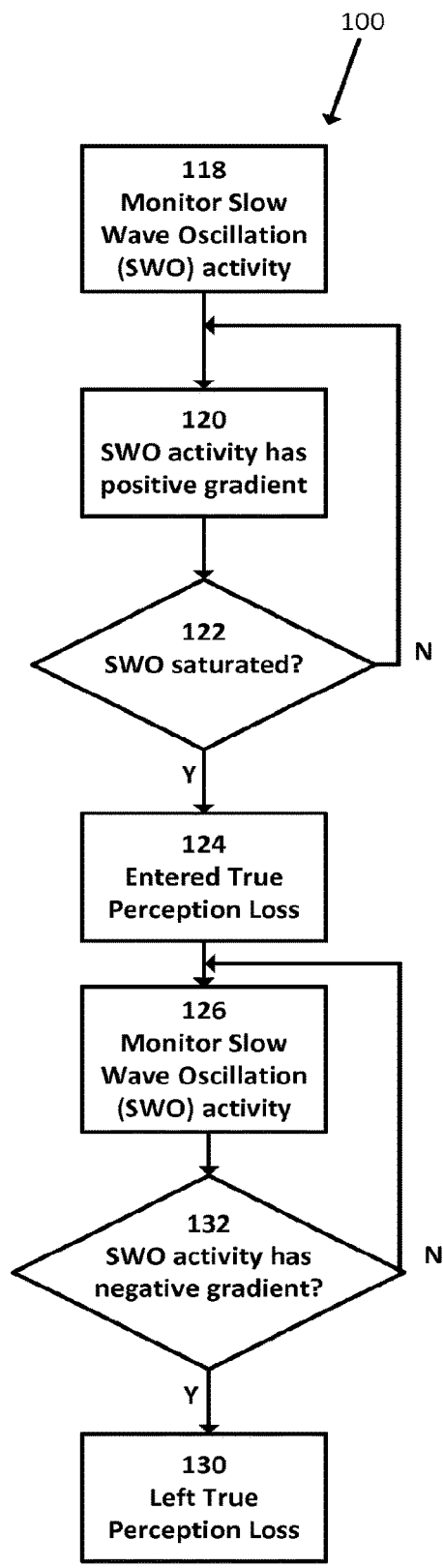
FIG. 4 shows a flowchart describing the steps of another example of the method of FIG. 1 where an intervention is used.

With reference to FIG. 4, another example of a method of detecting a neurophysiological marker for a state of true perception loss of a human is designated, generally, by the reference numeral 100. Method steps corresponding with those of the example 10 are designated by corresponding reference numerals. The method is executed using the electroencephalograph 14. The activity of the slow wave oscillations in the method 100 is determined in the same way as in the method 10.

Generally, the processor 18 monitors (Block 118) the activity of slow wave oscillations.

A positive gradient (Block 120) of the activity of the slow wave oscillations followed by the saturation (Block 122) of the slow wave oscillations is detected. The positive gradient is between 0 and 5 percent of the plateau level, per second (in the illustrated example: approximately between 2 and 6 percentage points per minute) and the activity at saturation is between 40 and 80 percent. The positive gradient may be dependent on (or affected by) the drug dosage regime or by other parameters, including those relating to the means by which true perception loss is induced, such as physiological factors, e.g. respiratory rate and heart rate, and/or psychological variables. On such detection, the point of saturation is identified (Block 124) as a marker for the human entering the state of true perception loss. Parameters dependent on the age, sex, surgical anxiety, trait anxiety, volume of grey matter of the frontal lobe of the human, recent sleep deprivation, sleep behaviour and sleep disorders (and other such factors) are queried from the database 19 to assist with the detection of the marker.

Slow Wave Oscillation (SWO) activity continues to be monitored, as previously performed (Block 118), during the true perception loss phase (Block 126).

The processor 18 also detects a marker for the human leaving the state of true perception loss in the form of a negative gradient (Block 132) of the activity of the slow wave oscillations following on the saturation of the slow wave oscillations. On such detection, the onset of the negative gradient is identified (Block 130) as a marker for the human leaving the state of true perception loss. The negative gradient is between 0 and 5 percent of the plateau level, per second (in the illustrated example: approximately between 2 and 6 percentage points per minute). The negative gradient may be dependent on (or affected by) the drug dosage regime or by other parameters, including those relating to the means by which true perception loss is induced, such as physiological factors, e.g. respiratory rate and heart rate, and/or psychological variables. Parameters dependent on the age, sex, surgical anxiety, trait anxiety, volume of grey matter of the frontal lobe of the human, recent sleep deprivation, sleep behaviour and sleep disorders are queried from the database to assist with the detection of the marker.

The values of the parameters are generally dependent on the maximum power of the slow wave oscillations on the scalp of the human. The parameters include a range of values per combination of age, sex, surgical anxiety, trait anxiety, volume of grey matter of the frontal lobe of the human, recent sleep deprivation, sleep behaviour and sleep disorders for the positive gradient, the level of saturation and the negative gradient, respectively. The volume in $cm^3$ of grey matter in the frontal lobe can be determined for example by MRI scan.

The experimental evidence as illustrated in FIGS. 5 to 13 demonstrates that slow wave oscillations are strongly related to the level of awareness of a human. It is envisaged that the activity of slow wave oscillations and the detection of slow wave activity saturation will be used as biomarkers for loss of and return to consciousness when it is impaired by drugs or pathology. Monitoring of slow wave activity provides a patient-specific target drug level for better anaesthesia management.

Although the experimental evidence was obtained from subjects anaesthetised using the anaesthetic propofol, it is envisaged that the method for detecting a state of true perception loss of a human can also be executed using other anaesthetics. In particular other anaesthetic agents that act via GABA(A) receptors cause similar activity of slow wave oscillations in the scalp electroencephalogram, with the activity reaching a maximum or saturation point (following loss of verbal responsiveness) under increasing exposure to the anaesthetic agent. Such anaesthetic agents include fluranes such as sevoflurane, isoflurane and desflurane and barbiturates such as thiopental. A combination of agents, combined in sequence or in administration or both, may be used for anaesthesia.

Potential uses of slow wave activity measurements and slow wave activity saturation detection include: titration of sedation and anaesthesia in operating theatres and intensive care units, development of new sedative or anaesthetic drugs and automated monitoring of sleep and guided scientific research at this now identified crucial time point to further our understanding of consciousness from a neuroscience perspective. Consciousness is so ubiquitous and important that the potential uses are widespread including but not limited to diagnosis and treatment of diseases of altered consciousness, development of new drugs, development of new strategies to improve consciousness and development of devices to detect alterations in the level of consciousness and vigilance.

Intra-individual variations in the saturation level may be correlated to anatomical brain factors, brain functional connectivity factors, and/or biochemical factors. For example in the case of propofol as anaesthetic agent, baseline GABA and glutamate brain neurotransmitter levels may be relevant biochemical factors. In a further example, connectivity between brainstem, cortical regions and/or brain lobes and cortical folding may be anatomical brain factors. These factors can assist prediction of the saturation level of a particular individual.

The procedure for determining the saturation time point and level of slow wave oscillations is now described in more detail.

For time-frequency analysis, the frequency power spectrum over time within the 0.5-30 Hz range is calculated using a multitaper spectral analysis (using Chronux®) with window size=3 s and step size=4s. Phasic changes in EEG absolute and relative power in the specific frequency bands of interest, i.e. beta (15-30 Hz), alpha (9-14 Hz), theta (4-8 Hz) and slow wave (0.5-1.5 Hz) bands, are calculated. Slow wave (SW) power time series are defined as the relative power in the slow wave range (0.5-1.5 Hz), also referred to hereinafter as slow wave activity (SWA). Activity is averaged across a plurality of channels. Temporal smoothing is carried out using a median filter of order 20.

Typically, activity (including SWA) is averaged across all available channels (each channel being associated with an electrode with particular montage coordinates—for example as illustrated in FIG. 2). In a variant, activity is associated with electrode location. This can provide information regarding activity in particular regions of the brain. In one example, frontal electrode channels are averaged, and parietal electrode channels are averaged, and frontal and parietal activity is compared. In another example, the activity at an individual electrode channel is compared to the activity as averaged across all available channels. In another example, the channels of neighbouring electrodes, bipolar measurements or any number of electrodes are compared. Bipolar or average referencing can be used to indicate both global and local changes respectively in electrical activity particularly in respect of slow wave and alpha band spectral changes. Voltage differences between individual electrodes particularly between frontal and parietal electrodes are used to determine true perception loss.

In order to identify the associated topographic distribution of the frequency specific changes, the average EEG power at each electrode coordinate is calculated for each frequency band across the experimental temporal region of interest using spline interpolation.

For blink artefact removal eye blinks are identified using an automated algorithm (BrainVision Analyser Version 2.0) that parses the VEOG channel. Independent component analysis (ICA) is used to remove blink artefact from the remaining EEG channels by constraining the data domain to the time interval around the blinks.

As a function of time, the SW power time course follows an S-shaped curve characterised by three intervals. First, a baseline period of low SW power, followed by a steady rise in SW power, and finally a period of plateau (slow wave activity saturation, or SWAS).

This time course is modelled using the following equation:

$$R(t) = a + \frac{b}{1 + \exp(-(t-c)/d)}$$

Where $\{a, b, c, d\}$ are free parameters that are fitted to the data. In the above, t denotes time (in minutes).

The first 2 parameters (a and b) are related to the activity levels at the baseline and SWAS.

Parameters c and d relate to the dynamics of the SWA time course (e.g. timing of the rise period).

The baseline and the SWAS levels are related to the free parameters via the equations:

$$R_{baseline} = R(-\infty) = a$$

$$R_{swas} = R(\infty) = a+b$$

The free parameters are optimised using a constrained optimisation routine (fmincon in Matlab®) that minimizes the sum-of-squared error between the model and the data Y:

$$E = \Sigma_t (Y(t) - R(t))^2.$$

Parameters are initialised as follows: a=perc(Y, 0.05), b=perc(Y, 0.95)−perc(Y, 0.05), c=25, d=3.5; where "perc" means percentile.

Parameters are constrained to be within the ranges: $1<a<100$; $1<b<100$; $1<c<100$; $1<d<10$.

Minimizing the above quantity (E) provides a Maximum Likelihood (ML) solution for the free parameters, and consequently gives an estimate of the SWA saturation level $R_{SWAS}$.

Figure 17:
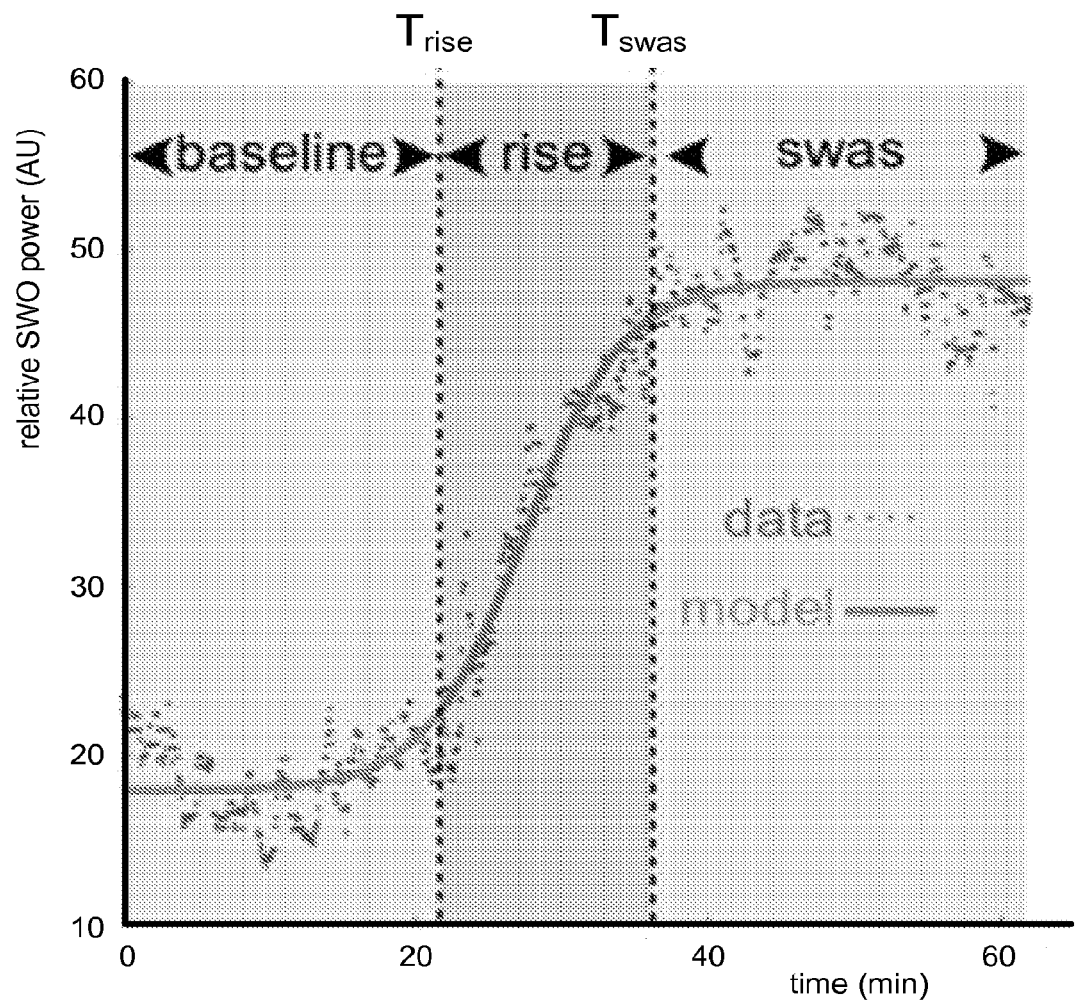
FIG. 17 shows an example of a slow wave power time course with a model fit.

FIG. 17 shows an example of a SW power time course from one subject over a 60 minute period. The three stages (baseline, rise, SWAS) can clearly be seen. The model fit is also shown in red.

Bayesian theory and the Laplace approximation are used to estimate confidence intervals on the SWA plateau and use these confidence intervals to estimate timings. The critical times that are to be estimated are $T_{rise}$ and $T_{SWAS}$ as indicated in FIG. 17.

In order to estimate the uncertainty of the estimated parameters, Bayesian inference is used. Let $\Omega$ denote the set of free parameters, i.e. $\Omega = \{a, b, c, d\}$. Bayes' theorem allows calculation of the posterior distribution of $\Omega$ give the data Y:

$$Pr(\Omega|Y) \propto Pr(Y|\Omega) Pr(\Omega).$$

The likelihood function $P(Y|\Omega)$ is given by (assuming Gaussian noise):

$$Pr(Y|\Omega) \propto \prod_t \exp\left(-\frac{0.5(Y(t) - R(t))^2}{\sigma^2}\right),$$

where σ2 is the noise variance, which is calculated empirically as the residual variance. The prior distribution $Pr(\Omega)$ is the uniform distribution. The Laplace approximation is used to calculate the posterior covariance matrix for the parameter set $\Omega$. This approximation takes the form:

$$Pr(\Omega|Y) \sim N(\Omega_{ML}, S).$$

This is a local approximation to the posterior distribution as a Gaussian distribution centred on the maximum likelihood solution (i.e. with mean $\Omega_{ML}$) and with covariance matrix $S=H-1*2*\sigma 2$, where H is the 4×4 matrix:

$$H = \begin{pmatrix} H_{aa} & H_{ab} & H_{ac} & H_{ad} \\ H_{ab} & H_{bb} & H_{bc} & H_{bd} \\ H_{ac} & H_{bc} & H_{cc} & H_{dc} \\ H_{ad} & H_{bd} & H_{cd} & H_{dd} \end{pmatrix}.$$

The elements of the above matrix are given by:

$$H_{xy} = \sum_t 2R_x(t)R_y(t) - 2(Y(t) - R(t))R_{xy}(t).$$

The above matrix depends on the first and second order derivatives of R(t) with respect to the parameters $\Omega=\{a,b,c,d\}$. These derivatives are given explicitly below (the matrix $R_{xy}$ being symmetric, only the lower diagonal elements are given).

$R_a=1$ $R_b=1/(X+1)$ $R_c=-(bX/(d(X+1)^2))$ $R_d=1(bX(c-t))/d^2(X+1)^2)$ $R_{aa}=0$ $R_{ab}=0$ $R_{ac}=0$ $R_{ad}=0$ $R_{bb}=0$ $R_{bc}=-X/(d(X+1)^2)$ $R_{bd}=(X(c-t))/(d^2(X+1)^2)$ $R_{cc}=(2bX^2)/(X+1)^3)-(Xb)/(d^2(X+1)^2)$ $R_{cd}=(Xb)/(d^2(X+1)^2)-(2bX^3(c-t)/(d^3(X+1)^3)+(Xb(c-t))/(d^3(X+1)^2)$ $R_{dd}=(2bX^2(c-t)^2)/(d^4(X+1)^3)-(bX(c-t)^2)/(d^4(X+1)^2)/(d^4(X+1)^2)-(2bX(c-t))/(d^3(X+1)^2)$

In the above equation, X is a function of time and is given by:

$$X(t) = \exp\left(\frac{c-t}{d}\right).$$

The above equations allow calculation of a local covariance matrix S for the model parameters. This matrix can be used to calculate the posterior variance for both baseline and SWAS. In calculating the elements of S, only the diagonal elements of H are used. This increases robustness in the online inference described below.

Since these two plateaus are linear combinations of the model parameters ($R_{baseline}=a$, $R_{SWAS}=a+b$), their marginal posterior distributions, under the Laplace approximation, are also Gaussian distributions. The standard deviations for the two plateaus are:

$\sigma_{baseline}=\sqrt{S(1,1)}$ $\sigma_{swas}=\sqrt{S(1,1)+S(2,2)}$

The above measures of standard deviation are used to determine the time point $T_{rise}$ that defines the moment where SW power starts increasing.

$T_{rise}$ is defined as the moment at which the current modelled time course exceeds the baseline estimate+2 standard deviations according to the Laplace approximation. FIG. 18 illustrates this. The SWA data 180 is used to obtain a best fit curve 182. The baseline estimate 184 has associated thereto an upper margin 186 of two standard deviations. $T_{rise}$ 188 is defined as the intersection of the best-fit curve 182 and the upper margin 186.

In order to determine the crucial moment at which SWAS occurs ($T_{SWAS}$), the real-time tracking is used for the following quantity:

$$f(t) = \frac{1}{1+X(t)},$$

where $X(t)=\exp((c(t)-t)/d(t))$ is as defined above in the offline model. The quantity f(t) varies between 0 and 1, and is closest to 1 when the plateau (SWAS) is reached.

$T_{SWAS}$ is determined to be the moment at which f(t) exceeds 0.9 with more than approximately 95% confidence (2 standard deviations). FIG. 19 illustrates this. f(t) 190 has associated thereto lower margin 192 of two standard deviations. $T_{SWAS}$ 196 is defined as the intersection of the 0.9 level 194 of f(t) 190 and the lower margin 192.

Confidence intervals on f(t) are calculated using error propagation theory. The time-dependent variance estimate for f(t) is given by the following formula:

$$\text{var}(f(t))=\sqrt{R_c^2 S(3,3)+R_d^2 S(4,4)},$$

where S is the covariance matrix for all four model parameters, as defined above. The partial derivatives $R_c$ and $R_d$ are given explicitly below:

$$R_c = -\frac{X(t)}{d(t)(1+X(t))^2},$$

$$R_d = \frac{X(c-t)}{d(t)^2(1+X(t))^2}.$$

Figure 20:
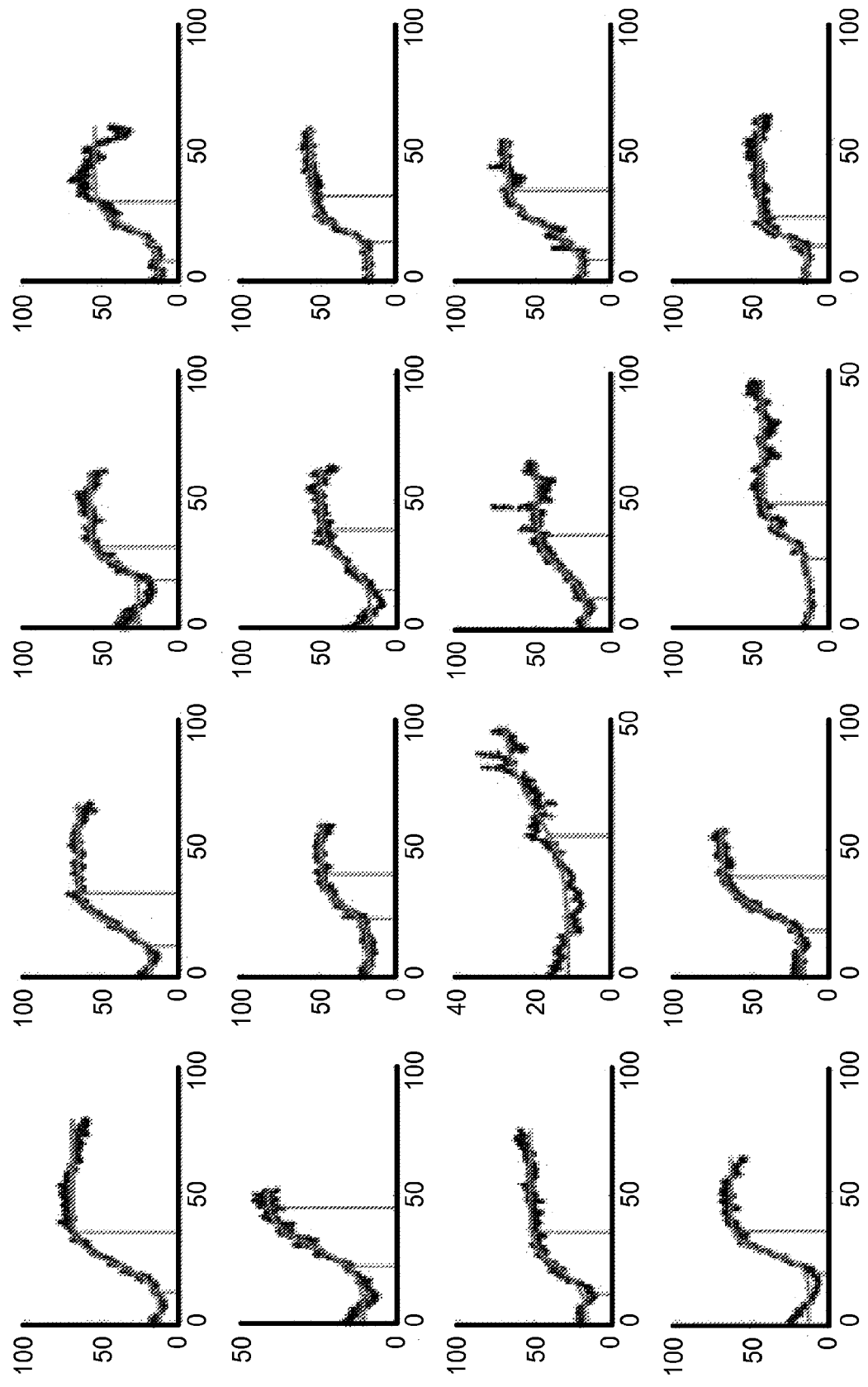
FIG. 20 shows timing parameter estimates in 16 subjects.

The robustness of this offline analysis is illustrated in FIG. 20 where the timing parameters are estimated in 16 subjects. The $T_{rise}$ and $T_{SWAS}$ times obtained by the algorithm are indicated with vertical lines. Comparison with the relatively noisy SWA data shows that the analysis results represent a reasonable selection of $T_{rise}$ and $T_{SWAS}$.

The algorithm described above uses pre-recorded data. The same model can be used for real time analysis of SWA data to enable real time monitoring of the response of subjects as they receive anaesthetic agent. In this case, the data can be analysed sequentially (sequential learning), where every new data point is used to update the posterior distribution as follows:

$Pr(\Omega|Y_1,Y_2,\ldots,Y_{n-1},Y_n) \propto Pr(\Omega|Y_1,Y_2,\ldots,Y_{n-1})Pr(Y_n|\Omega).$ Essentially, the posterior distribution given data points $\{Y_1,\ldots Y_{n-1}\}$ becomes the prior distribution when a new data point arrives.

Since the first few data points contain little information about the overall shape of the data (e.g. the SWAS plateau), informative priors on the model parameters are required.

Gaussian priors for all four parameters (a priori independent) are used as follows:

$$Pr(a,b,c,d)=Pr(a)Pr(b)Pr(c)Pr(d)=N(m_a,s_a)N(m_b,s_b)N(m_c,s_c)N(m_d,s_d),$$

where: {ma,mb,mc,md}={16, 38, 24, 3.5} and {sa,sb,sc,sd}={4, 10, 4, 1}. These values come from fitting the offline model (with uniform priors) to 16 subjects and taking the mean and standard deviations of the fitted parameters as priors for sequential data on a new subject.

In this sequential learning, parameter estimate are functions of time (i.e. a=a(t), b=b(t), c=c(t), d=d(t)). Therefore, model predictions and predictions for the two plateaus also vary with time.

Figure 23:
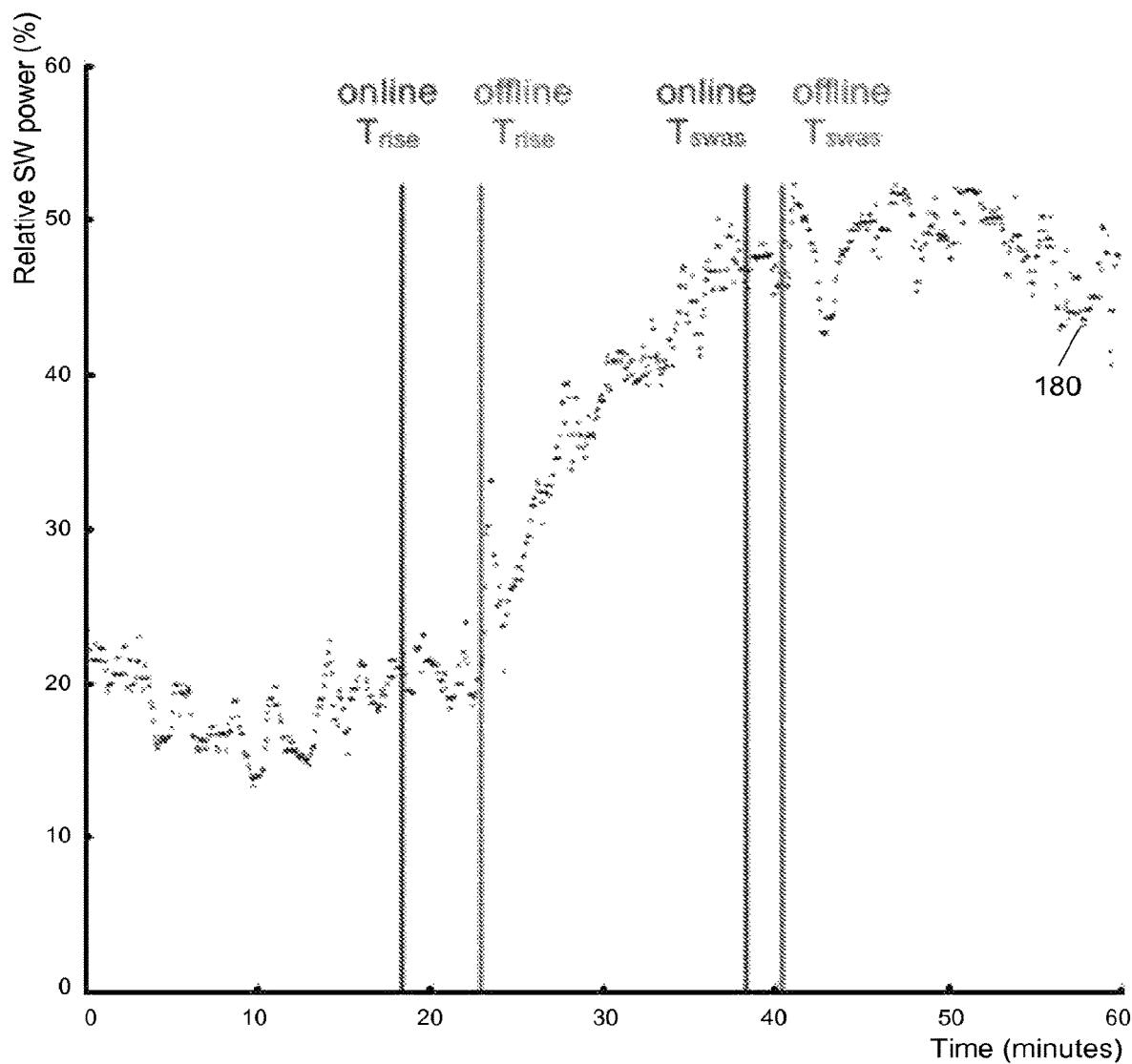
FIG. 23 shows a comparison of the onset of a gradient and the saturation point in slow wave data for online and offline data analysis.

$T_{rise}$ and $T_{SWAS}$ are defined in the same way as in the offline estimation, but this time using real-time estimates of the free parameters. FIGS. 21 and 22 show comparisons of the curve fits and estimate for online data analysis (upper panels) and offline data analysis (lower panels, as in FIGS. 18 and 19) and of these timings. FIG. 23 shows a comparison between online and offline timing estimates. In the illustrated sample data set the online estimates are both earlier than the corresponding offline estimates.

The formula for the diagonal elements of S is different from the offline inference, because of the introduction of informative Gaussian priors:

$$S_{xx} = \left(\frac{H_{xx}}{2\sigma^2} + \frac{1}{\sigma_x^2}\right)^{-1}.$$

The algorithm for estimating online parameters and timings is outlined below.

```
- Initialise Ω: Ω=prior means, Current interval='baseline'
- For every new time point:
    * Add new data point and update posterior distribution
    * Update model prediction
    * Calculate covariance matrix S using Laplace approximation
    * Calculate baseline variance and var(f(t)) using error propagation
        - If model prediction > baseline+2*std(baseline)
            >> Current interval=Rising
            >> T_rise=current time
        - If f(t)+2*std(f(t))>0.95
            >> Current interval=Saturation
            >> T_SWAS = current time
```

With the online data analysis described above, it is possible to monitor the real-time response of a subject to an anaesthetic agent, and adapt the dose of the anaesthetic agent so as to maintain the dosage such that the slow wave activity is at or near the described slow wave saturation plateau. This has the advantage of ensuring the patient is optimally anaesthetised, with neither a greater dose than necessary (which can affect post-operative recovery with both short- and long-term effects on morbidity and mortality), nor a dose that is too low (which can be associated with intraoperative awareness, causing long-term psychiatric burden).

A system for maintaining an optimal anaesthetic dosage to ensure that the slow wave activity is at or near the described slow wave saturation plateau is now described in more detail.

The system can operate in two modes: closed-loop and non-closed loop. The closed-loop system uses the measured SWA (and also alpha oscillations) to alter the drug dose so that SWAS targeting is achieved. The non-closed loop system allows monitoring of the EEG SWA so that alteration of drug dose and targeting can be achieved manually, for example similar to a bispectral index monitor. The two modes can enable flexibility for clinical need and the natural oscillation of drug dose required due to increases in nociceptive input or pharmacological drift. The closed-loop system can have a permanent manual over-ride if required.

Figure 25:
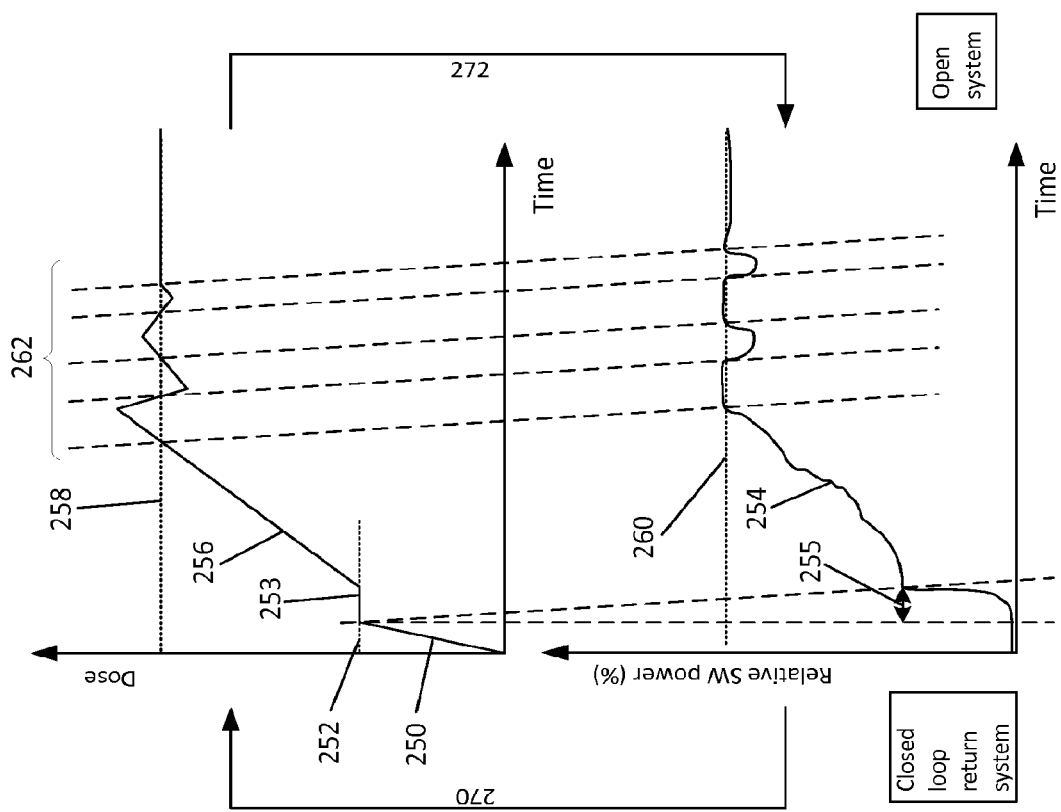
FIG. 25 shows dose and relative slow wave activity against time for an anaesthetic drug with delayed effect.
Figure 24:
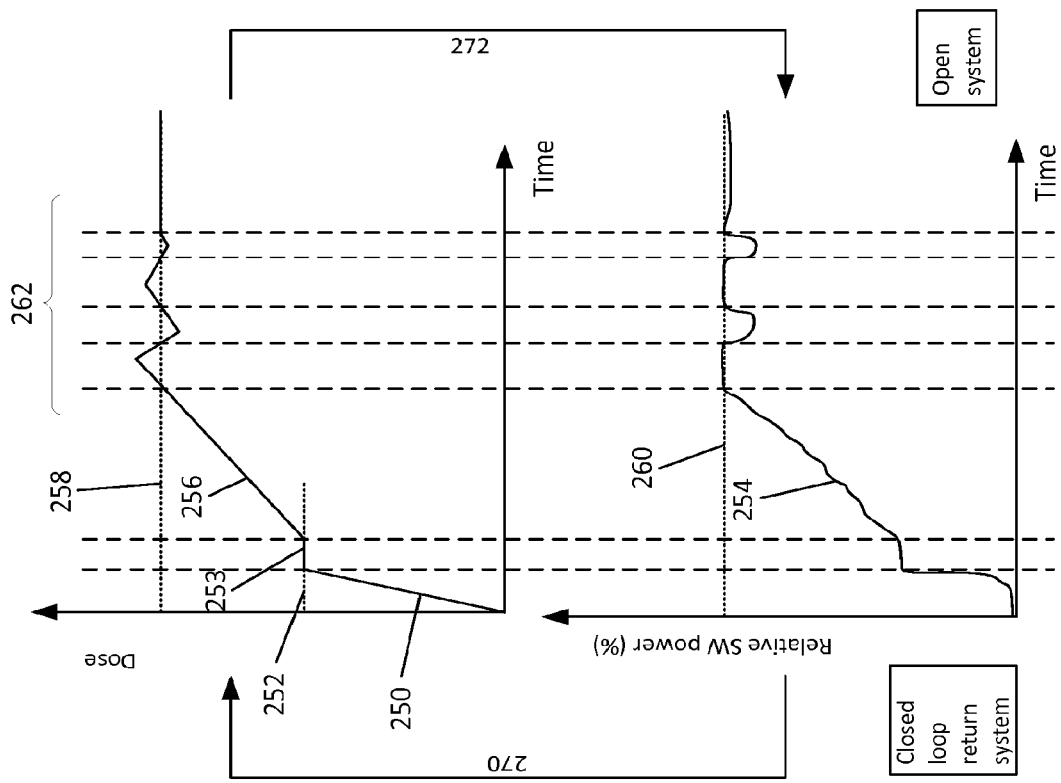
FIG. 24 shows dose and relative slow wave activity against time for an anaesthetic drug with near-instantaneous effect.

FIGS. 24 and 25 show in the upper panel a graph charting dose (e.g. drug administration rate, or anaesthetic level, or effective site concentration) against time. In the lower panel the simultaneously detected relative slow wave activity is charted against time. In FIG. 24, an example is illustrated for an anaesthetic drug with pharmacodynamics and pharmacokinetics that produce a near-instantaneous (or at least very rapid) effect of dose on SWA. In FIG. 25, an example is illustrated for an anaesthetic drug with pharmacodynamics and pharmacokinetics that produce a delayed effect of dose on SWA. Such a delay can be taken into account in the system to ensure the SWAS is determined correctly. The analysis of the detected relative slow wave activity informs 270 the dosage, and the dosage influences 272 the SWA.

Steps for closed-loop anaesthetic monitoring to find an optimum dose include:

1. Check integrity of EEG signals, e.g. loose electrodes, out of range or low voltages. Set up EEG electrode referencing configuration accordingly, for example bipolar, average, referential and/or Laplacian referencing. Alter expected voltage ranges and apply appropriate scaling of electrical parameters (including definitions and burst suppression ratios) for patients with low voltage EEG signals.
2. Enter patient profile (e.g. age, sex, weight, surgical anxiety profile, trait anxiety profile, previous anaesthetic history (including immediate pre-operative anaesthetic history), etc.) into system.
3. Enter anaesthetic drug to be used. This loads a suitable population based pharmacokinetic/dynamic model and provides an expected range for SWAS based on the average dose response, giving an idea of the SWAS levels for this drug in an individual of the specified patient profile, including age and weight. The pharmacokinetic/dynamic model can also be used to determine effective site concentration in dependence on drug administration rate.
4. Determine starting anaesthetic dose 252 using database and clinical experience (particularly dealing with comorbidities) and start rapid infusion 250 to this level 252. The starting dose 252 is well below the expected saturation level for the given individual. In the examples illustrated in FIGS. 24 and 25 during the rapid infusion phases 250 initially little effect on SWA is seen before SWA begins to increase. A lag phase 253 can be included where the dose is maintained at the starting dose level 252, for example to allow stabilisation of the slow wave activity, and/or to evaluate a delay 255 between drug administration and drug effect on SWA. The lag phase 253 can cause the SWA to display a plateau, which is however not the SWAS (because it is not a maximum plateau, and saturation is not achieved, but a further increase of dose causes the SWA to increase further).
5. A slower dose ramp 256, which is determined depending on the initial starting drug dose 252 and a drug pharmacokinetic/pharmacodynamic model, is then used to approach SWAS. In the examples illustrated in FIGS. 24 and 25 during the slower dose ramp phases 256 the SWA increases 254.

6. During the slower dose ramp phase 256 the Bayesian SWAS detection algorithm described above is used to analyse and monitor the EEG recordings to detect increasing slow wave activity levels whilst concurrently monitoring the burst suppression ratio (see step 7 below). The real time algorithm indicates when the relative power in the SW band increases and in particular provides an indicator that can indicate when the SWA is exhibiting an increasing slope. When the SWAS level 260 is achieved, it is possible to alter the drug dosage (e.g. alter the rate of drug delivery) to provide fine-tuning of the dose to the optimum dose 258 (the optimum dose 258 being at or slightly above or near the level at which SWAS occurs). This fine-tuning (or 'stair-casing') stage 262 can take into account the pharmacodynamics and pharmacokinetics of the given anaesthetic drug and the step size can be altered accordingly to account for the appropriate rate constants for transference across the blood-brain barrier and redistribution of the drug through the body tissues. In the fine-tuning stage 262 a near-optimum dosage is seen, with the dosage rate increasing and decreasing around the optimum dose 258. A decrease below the optimum dose 258 causes the SWA to drop below the SWAS 260, and an increase at or above the optimum dose 258 causes the SWA to remain at the SWAS 260. Hence as the dose fluctuates around the optimum dose 258, the SWA temporarily dips below the SWAS. In the fine-tuning (or 'stair-casing') stage 262 the dose initially overshoots the optimum dose 258, and then once saturation is observed the dose is allowed to drop below the optimum dose 258 again. Once the SWA drops below saturation again, the dose is increased again so as to overshoots the optimum dose 258, with a lesser overshoot than in the foregoing iteration. The process is repeated to iteratively approach the optimum dose 258 with increasing precision.

7. Concurrent monitoring of the burst suppression ratio occurs. Burst suppression is characterized by alternating periods of bursts and suppressed or isoelectric EEG. Suppression periods can be defined as low voltage EEG periods of greater than 0.5 seconds duration with amplitudes of ±5 microvolts. The overall power can be evaluated for burst suppression analysis, or only the power in a particular band. The burst suppression ratio BSR is defined as the fraction of time in the suppressed state compared with the total epoch length under investigation, with a burst suppression ratio of 100% signalling EEG silence. The relative SWA amplitude below which suppression is assumed can be adjusted depending on the quality of the initial signal. The measurement window or epoching used for BSR assessment also depends on context dependent/elimination half-life of the drug so can be altered on this basis.

8. As burst suppression occurs at doses >SWAS, if the BSR is above a threshold this indicates that the delivered drug dose is in excess of the required quantity. The value of the BSR and knowledge of the individual's SWAS response profile from the Bayesian algorithm dose indicates the step size, having adjusted for the specific drug pharmacokinetic and pharmacodynamic model.

9. Once the SWAS level for this individual has been determined this value is stored in the associated database so that SWAS can be determined more quickly in this individual for future anaesthetics and can also be used to improve the population estimation of the SWAS ranges to reduce morbidity and mortality.

10. Emergence of the subject can be estimated based on the specific drug pharmacokinetic and pharmacodynamic model. Other factors, including the observed SWA, can be taken into account for predicting the emergence of the subject.

In a variant, the dosage is maintained at a level above the optimum dose 258 associated with the SWAS described above, and at a level that is associated with a particular BSR threshold.

In a variant, the rate of drug administration is optimised with respect to the effect on the SWA response. For example, a high rate of drug administration can cause a hysteresis between SWAS and optimum dose, and a lower rate of drug administration is more favourable in order to determine the optimum dose. Subject factors can also be used to inform the drug administration. For example, an anxious subject may require a higher dose for loss of consciousness, and the starting dose 252 and slower dose ramp phase 256 can be adjusted to an anticipated higher dose at SWAS.

In a variant, a number of different priors associated with different possible subject characteristics (such as age, sex, volume of grey matter of the frontal lobe, surgical anxiety, trait anxiety, previous anaesthetic history, recent sleep deprivation, sleep disorders and sleep behaviour) is stored in a database and for a particular subject profile the most suitable prior is determined and selected. The selected prior is then used in the Bayesian SWAS detection algorithm.

In a variant, the prediction of behaviour during emergence from loss of consciousness is based on observation of the SWA during induction of loss of consciousness. For example, the gradient of SWA increase at induction is considered to estimate the SWA decrease which is used to characterise emergence. In another example the dose-SWAS hysteresis at the end of induction is considered to estimate hysteresis at the start of emergence. Subject information can be used to inform the prediction of the individual's SWAS response profile, optionally by way of a pharmacokinetic and pharmacodynamic model adapted to subject information. In this manner subject information can be used to predict, for example, whether induction in and emergence from loss of consciousness follow similar or dissimilar SWA behaviour, and how the SWA behaviour is expected to be dissimilar. For example, an anxious subject may display relatively slow induction, and relatively fast emergence. The use of subject information can enable more accurate and reliable prediction of emergence behaviour based on observation of the SWA during induction.

In a variant, information from the alpha frequency band is evaluated to increase the confidence in the Bayesian SWAS detection algorithm. In particular, factors such as saturation of alpha band activity, power proportion in the alpha band, and spindle activity can be evaluated. The evaluation of information from the alpha frequency band can provide a further indication, alongside the evaluation of the SWA information, for loss of consciousness and optimum drug dose. The indicators can be combined into a single indicator, or they can be considered separately. The indicators can be considered reliable only if both agree, or one indicator can be overridden by another. The optimum indicator with the best confidence can depend on subject parameters.

In a variant, SWA is associated with electrode location. This can for example provide an indication that, although global SWAS is observed, in a particular region of the brain SWAS is not yet achieved. In this case for example the dose can be increased above what might otherwise be considered the optimum dose. In another example it may be determined that the optimum dose is achieved when parietal SWAS is observed. In another example it may be determined that the optimum dose is achieved when frontal alpha band activity saturation is observed.

In a variant, a combination of anaesthetics is administered to the subject. For example, if the combination is maintained throughout the procedure (e.g. a certain proportion of propofol is combined with a certain proportion of flurane at all times), then the optimum dose for the combination is found analogous to the case of using a single anaesthetic agent. In another example, a first anaesthetic (such as propofol) is used for induction of anaesthesia, and a second anaesthetic (such as flurane) is used for maintenance of anaesthesia after loss of perception. In this case, the first anaesthetic is administered up until SWAS is observed, same as in the case of using a single anaesthetic agent. Thereafter, the dose of the first anaesthetic is reduced while the dose of the second anaesthetic is increased. To ensure that the optimum drug dose is maintained, a conversion can be used that specifies equivalence of a certain dose of the first anaesthetic to an appropriate dose of the second anaesthetic, with assistance of known data from the database. Alternatively or additionally, the maintenance of anaesthesia includes periods in which the dose slightly overshoots the optimum dose and then SWAS is observed, and periods in which the dose drops slightly below the optimum dose and then the SWA drops below saturation again. As the anaesthetic composition changes, the dosage is adapted to maintain fluctuation of the SWA about the SWAS.

In a variant, a Kalman filter is used for the SWAS detection algorithm in place of the Bayesian SWAS detection algorithm described above, particularly for maintenance at SWAS once the saturation level has been determined.

Data recorded for individual subjects is subject to an offline analysis to determine the SWAS level and along with other inter-individual characteristics (e.g. from magnetic resonance as well as accompanying operative and anaesthetic data) are uploaded to a central database to allow better estimation of the predicted dose for SWAS to occur (for the initial phases).

Figure 26:
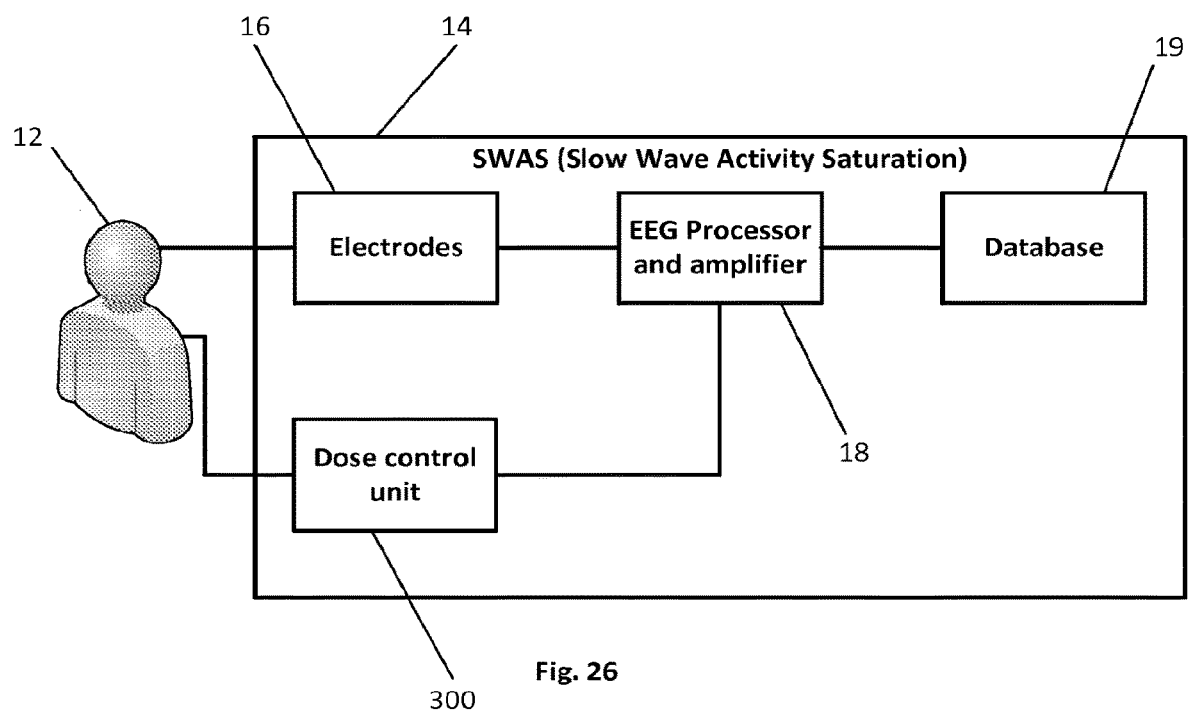
FIG. 26 shows a SWAS system with a dose control unit.

FIG. 26 shows a SWAS system 14 with a dose control unit 300 for maintaining an optimal anaesthetic dosage to ensure that the slow wave activity is at or near the described SWAS plateau as described above.

Figure 27:
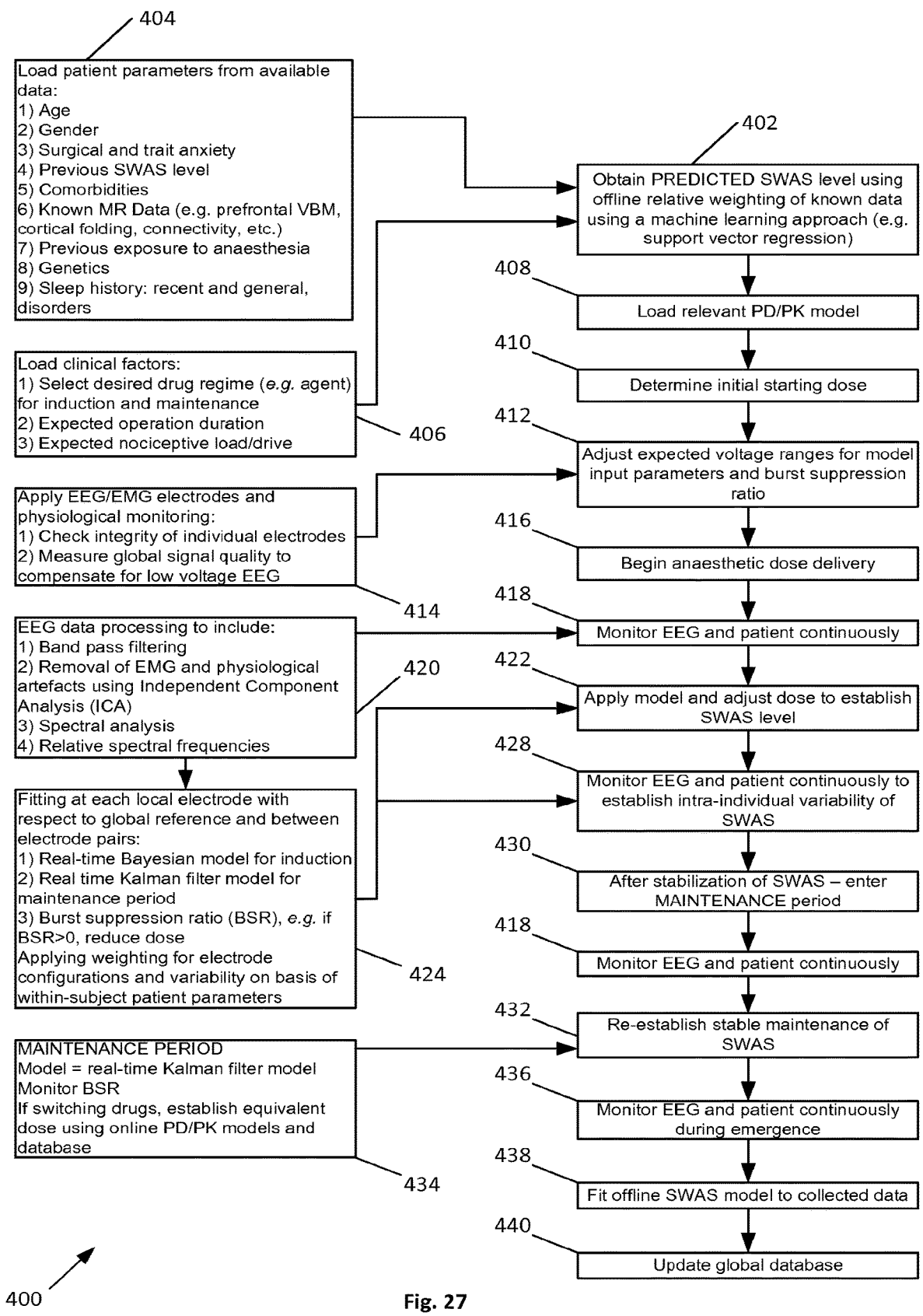
FIG. 27 shows a flowchart illustrating an exemplary the procedure followed by a SWAS system.

FIG. 27 shows a flowchart exemplifying a procedure followed by a SWAS system 14. Offline data relating to inter-individual characteristics and patient parameters 404 is retrieved and input to predict a SWAS level 402 for a given patient using offline known data relating to relevant parameters 404 in the database. Such parameters 404 can include age, gender, surgical anxiety, trait anxiety, historical SWAS level, comorbidities, known MR data (such as anatomical connectivity of the brain, cortical folding, prefrontal VBM, neurotransmitter levels, etc.), history of exposure to anaesthesia, genetic aspects of phenotype handling of anaesthesia, sleep history (including disorders, recent and general behaviour), etc.

The prediction of the SWAS level is further informed by parameters relating to clinical factors 406, which are loaded into the SWAS prediction 402. Clinical factors can include the desired drug regime (e.g. agent) for induction and maintenance on unconsciousness, expected operation duration, expected nociceptive load and/or drive, etc. SWAS prediction 402 uses a relative weighting of loaded parameters (patient parameters 404 and clinical parameters 406) and machine learning, such as support vector regression, to support the weighting of parameters.

Having derived a prediction of the SWAS level for the given patient 402, relevant pharmacodynamics and pharmacokinetics model data is loaded 408 in order to determine an initial starting drug dose 410.

Psychological and physiological monitoring begins 414 once the appropriate instrumentation is connected to the patient, e.g. EEG, EMG, etc. The integrity of the EEG signal is checked across each of the electrodes, e.g. loose electrodes, out of range or low voltages. EEG electrode configuration and referencing are accordingly set up, for example bipolar, average, referential and/or Laplacian referencing. Global signal quality of the psychological and/or physiological monitoring can be performed and appropriate scaling of electrical parameters (including definitions and burst suppression ratios) applied for patients with low voltage EEG signals. For these patients low global averages are used as an indicator with scaling applied to some of the electrical parameters accordingly including definitions of burst suppression ratios. The psychological and physiological monitoring information 414 is used to adjust expected EEG voltage ranges for the patient 412 according to the patient, model and burst suppression parameters.

Anaesthetic dose delivery can consequently begin 416 and psychological and physiological monitoring of the patient continues 418. The patient's EEG response is analysed and processed 420, for example by using, spectral analysis, relative spectral frequency, filtering (e.g. using a band pass), etc. Removal of artefacts due to physiological activity, such as muscle activation (a known cause of artefacts in the delta band), cardiac activity, glossokinetics, eye movements, blinking, etc., can also be performed, for example using Independent Component Analysis (ICA) from EEG, EMG and/or ECG, etc. information 420.

Patient psychological and/or physiological information from the patient is analysed throughout the process using models for real-time Bayesian induction, real-time Kalman filtering models for the maintenance period, burst suppression ratios to determine dose output and weighting of electrode configuration to account for variability of intra-subject patient parameters 424. Such analysis of patient psychological and/or physiological information 424 is used to derive dose control to adjust the output of the anaesthetic drug to the patient in order to establish the SWAS level 422. The patient continues to be monitored and drug dosage output controlled, according to patient psychological and/or physiological information analysis 424, to accommodate intra-individual variability of the SWAS 428.

When the SWAS level has stabilised the patient has entered the maintenance period 430 and monitoring of the patient continues 418. Should monitoring of the patient indicate instability in the SWAS an attempt is made to re-establish stable maintenance of SWAS by adjusting the dose output 432 according to a maintenance period regimen 434. The maintenance period regimen 434 analyses patient monitoring information, inform any readjustment of dosage in order for the patient to remain in the maintenance phase, this is performed by considering a number of factors including real-time Kalman filtering, burst suppression ratio and, if appropriate, calculate equivalent dose values by using online pharmacodynamics and pharmacokinetics models and databases, if the drug switching occurs 434.

Monitoring of the patient continues into the emergence phase 436.

Data from the monitoring of the patient, which is recorded throughout the previous steps, is fit to the offline SWAS model 438. The global database of data and model fitting is subsequently updated to incorporate any recorded data 440 and new offline data is thereby generated to improve SWAS modelling.

It will be understood that the present invention has been described above purely by way of example, and modifications of detail can be made within the scope of the invention.

Reference numerals appearing in the claims are by way of illustration only and shall have no limiting effect on the scope of the claims.

The invention claimed is:

1. A human brain activity monitoring apparatus for discerning in real-time a state of true perception loss in a human undergoing anaesthesia under administration of an anaesthetic agent, where the dose of the anaesthetic agent is varied,
the apparatus comprising a processor configured to execute the steps of:
receiving in real-time electrical signals from a plurality of sensors arranged to sense electrical brain activity of a human;
transforming in real-time the electrical signals into the frequency domain;
processing in real-time the electrical signals to determine an activity of electrical oscillations in a slow wave spectral band between 0 Hz and 5 Hz;
evaluating in real-time a rate of change over time of said activity in the slow wave spectral band;
determining in real-time when the rate of change of said activity in the slow wave spectral band drops below a predetermined threshold; and
providing an indication of a human having entered a true state of perception loss when said rate of change drops below the predetermined threshold.

2. The apparatus of claim 1 wherein the predetermined threshold is at or near zero.

3. The apparatus of claim 1 wherein the processor is further configured to execute the steps of:
determining when the rate of change of said activity in the slow wave spectral band drops below a further predetermined threshold; and
providing an indication of a human having left a true state of perception loss when said rate of change drops below the further predetermined threshold.

4. The apparatus of claim 3 wherein the further predetermined threshold is at or near zero.

5. The apparatus of claim 1 wherein the processor is further configured to execute the steps of:
receiving dose information specifying the variation of the dose of the anaesthetic agent;
determining whether the rate of change of said activity dropping below a predetermined threshold is in response to a dose variation stopping; and
providing the indication of a human having entered a true state of perception loss only if the drop below the predetermined threshold is in response to a varying dose of the anaesthetic agent.

6. The apparatus of claim 5 wherein the processor is further configured to execute the step of:
determining a delay between administration of anaesthetic agent and effect on said activity.

7. The apparatus of claim 5 wherein the processor is further configured to execute the step of:
determining an optimum dose of anaesthetic agent, wherein the optimum dose is the, or near, minimum dose required to induce a state of true perception loss.

8. The apparatus according to claim 1, wherein the activity is the power of the electrical signals in the slow wave spectral band as a percentage of the power of the electrical signals in a broad spectral band, preferably between 0 Hz and 50 Hz.

9. The apparatus according to claim 1, wherein the processor is further configured to execute the steps of:
determining a burst suppression ratio based on a fraction of time the electrical signals have a low oscillation amplitude; and
providing an indicator of a human having exceeded a dose of the anaesthetic agent required to enter a true state of perception loss when said burst suppression ratio rises above a predetermined threshold.

10. The apparatus of claim 9 wherein a low oscillation amplitude is an oscillation amplitude in the range of ±10 microvolts, ±5 microvolts, or ±2 microvolts.

11. A human brain activity monitoring method for discerning a state of true perception loss in a human undergoing anaesthesia under administration of an anaesthetic agent, where the dose of the anaesthetic agent is varied, the method comprising:
receiving at a processor in real-time electrical signals from a plurality of sensors arranged to sense electrical brain activity of a human;
processing in real-time, by the processor, the electrical signals to determine an activity of electrical oscillations in a slow wave spectral band between 0 Hz and 5 Hz;
evaluating in real-time, by the processor, a rate of change over time of said activity in the slow wave spectral band;
determining in real-time, by the processor, when the rate of change of said activity in the slow wave spectral band drops below a predetermined threshold; and
providing, by the processor, an indication of a human having entered a true state of perception loss when said rate of change drops below the predetermined threshold.

12. The method of claim 11 wherein the predetermined threshold is at or near zero.

13. The method of claim 11 further comprising:
determining, by the processor, when the rate of change of said activity in the slow wave spectral band drops below a further predetermined threshold; and
providing an indication of a human having left a true state of perception loss when said rate of change drops below the further predetermined threshold;
optionally wherein the further predetermined threshold is at or near zero.

14. The method of claim 11 further comprising:
receiving, at the processor, dose information specifying the variation of the dose of the anaesthetic agent;
determining, by the processor, whether the rate of change of said activity dropping below a predetermined threshold is in response to a dose variation stopping; and
providing, by the processor, the indication of a human having entered a true state of perception loss only if the drop below the predetermined threshold is in response to a varying dose of the anaesthetic agent.

15. The method of claim 14 further comprising:
determining, by the processor, a delay between administration of anaesthetic agent and effect on said activity.

16. The method of claim 14 further comprising:

determining, by the processor, an optimum dose of anaesthetic agent, wherein the optimum dose is the, or near, minimum dose required to induce a state of true perception loss.

17. The method of claim 11, wherein the activity is the power of the electrical signals in the slow wave spectral band as a percentage of the power of the electrical signals in a broad spectral band, preferably between 0 Hz and 50 Hz.

18. The method of claim 11 further comprising:

determining, by the processor, a burst suppression ratio based on a fraction of time the electrical signals have a low oscillation amplitude, preferably a low oscillation amplitude being in the range of ±10 microvolts, ±5 microvolts, or ±2 microvolts; and providing, by the processor, an indicator of a human having exceeded a dose of the anaesthetic agent required to enter a true state of perception loss when said burst suppression ratio rises above a predetermined threshold.

19. A computer readable medium having program code adapted to, when executed on a computer, perform the method of claim 11.

20. A human brain activity monitoring device for discerning a state of true perception loss of a human while the human is being administered an anaesthetic agent, the device comprising:

a receiver configured to receive sensed electrical signals indicative of real-time brain activity of the human from one or more sensors;

a processor configured to determine in real-time an activity of oscillations present in the electrical signals, wherein the oscillations are slow wave oscillations in a spectral band between 0 Hz and 5 Hz, wherein the processor is further configured to determine in real-time a rate of change of the activity of oscillations, and wherein a zero, or near zero, rate of change suggests a state of true perception loss; and an indicator configured to provide an indication of a human having entered a true state of perception loss when the rate of change is at or near zero.

* * * * *